US008721630B2

(12) United States Patent
Ortiz et al.

(10) Patent No.: US 8,721,630 B2
(45) Date of Patent: May 13, 2014

(54) METHODS AND DEVICES FOR CONTROLLING ARTICULATION

(75) Inventors: Mark S. Ortiz, Milford, OH (US); Frederick E. Shelton, IV, Hillsboro, OH (US); James T. Spivey, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1003 days.

(21) Appl. No.: 11/277,323

(22) Filed: Mar. 23, 2006

(65) Prior Publication Data

US 2007/0221700 A1 Sep. 27, 2007

(51) Int. Cl.
*A61B 17/00* (2006.01)
*A61B 1/00* (2006.01)

(52) U.S. Cl.
USPC .................................. 606/1; 600/142

(58) Field of Classification Search
USPC .............. 600/129, 141–150, 104; 606/208, 1, 606/205
See application file for complete search history.

(56) References Cited

U.S. PATENT DOCUMENTS

| | | | |
|---|---|---|---|
| 3,643,851 | A | 2/1972 | Green et al. |
| 3,662,939 | A | 5/1972 | Bryan |
| 3,717,294 | A | 2/1973 | Green |
| 3,734,207 | A | 5/1973 | Fishbein |
| 3,819,100 | A | 6/1974 | Noiles et al. |
| 3,892,228 | A | 7/1975 | Mitsui |
| 3,894,174 | A | 7/1975 | Cartun |
| 3,940,844 | A | 3/1976 | Colby et al. |
| 4,207,898 | A | 6/1980 | Becht |
| 4,213,562 | A | 7/1980 | Garrett et al. |

(Continued)

FOREIGN PATENT DOCUMENTS

| | | |
|---|---|---|
| CA | 245894 A | 1/1925 |
| CA | 2512960 A1 | 1/2006 |

(Continued)

OTHER PUBLICATIONS

Paul Breedveld, et al., "A New, Easily Miniaturized Sterrable Endoscope," IEEE Engineering in Medicine and Biology Magazine (Nov./Dec. 2005).

(Continued)

*Primary Examiner* — Alireza Nia
(74) *Attorney, Agent, or Firm* — Nutter McClennen & Fish LLP

(57) ABSTRACT

Methods and devices are provided for controlling movement of a working end of a surgical device. In one embodiment, methods and devices are provided for moving an end effector on a distal end of a surgical fastening device. Movement can include rotational movement of the end effector about an axis of the shaft, articulation of the end effector relative to the shaft, and actuation of an end effector, e.g., closing, firing, and/or cutting. In other embodiments, a single cable actuator is provided and is movable between a first position, in which it is effective to rotate an end effector without actuating (i.e., closing and firing) the end effector, and a second position, in which it is effective to actuate the end effector without rotating the end effector. In other aspects, methods and devices are provided for moving a flexible neck formed on a distal end of an accessory channel for use with an endoscope. Movement of the flexible neck can be used to control positioning of a tool extending through the flexible neck.

25 Claims, 21 Drawing Sheets

(56) References Cited

U.S. PATENT DOCUMENTS

| | | | |
|---|---|---|---|
| 4,331,277 A | 5/1982 | Green | |
| 4,349,028 A | 9/1982 | Green | |
| 4,383,634 A | 5/1983 | Green | |
| 4,402,445 A | 9/1983 | Green | |
| 4,415,112 A | 11/1983 | Green | |
| 4,454,887 A | 6/1984 | Kruger | |
| 4,475,679 A | 10/1984 | Fleury, Jr. | |
| 4,500,024 A | 2/1985 | DiGiovanni et al. | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,605,001 A | 8/1986 | Rothfuss et al. | |
| 4,606,343 A | 8/1986 | Conta et al. | |
| 4,608,981 A | 9/1986 | Rothfuss et al. | |
| 4,610,383 A | 9/1986 | Rothfuss et al. | |
| 4,629,107 A | 12/1986 | Fedotov et al. | |
| 4,646,722 A | 3/1987 | Silverstein et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,728,876 A | 3/1988 | Mongeon et al. | |
| 4,729,260 A | 3/1988 | Dudden | |
| 4,754,909 A | 7/1988 | Barker et al. | |
| 4,767,044 A | 8/1988 | Green | |
| 4,790,225 A | 12/1988 | Moody et al. | |
| 4,869,414 A | 9/1989 | Green et al. | |
| 4,869,415 A | 9/1989 | Fox | |
| 4,880,015 A | 11/1989 | Nierman | |
| 4,892,244 A | 1/1990 | Fox et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 5,027,834 A | 7/1991 | Pruitt | |
| 5,031,814 A | 7/1991 | Tompkins et al. | |
| 5,040,715 A | 8/1991 | Green | |
| 5,084,057 A | 1/1992 | Green et al. | |
| 5,088,979 A | 2/1992 | Filipi et al. | |
| 5,100,420 A | 3/1992 | Green et al. | |
| 5,195,968 A | 3/1993 | Lundquist et al. | |
| 5,211,649 A | 5/1993 | Kohler et al. | |
| 5,259,366 A | 11/1993 | Reydel et al. | |
| RE34,519 E | 1/1994 | Fox et al. | |
| 5,376,095 A | 12/1994 | Ortiz | |
| 5,381,782 A * | 1/1995 | DeLaRama et al. | 600/149 |
| 5,383,880 A | 1/1995 | Hooven et al. | |
| 5,397,046 A | 3/1995 | Savage et al. | |
| 5,431,322 A | 7/1995 | Green et al. | |
| 5,433,721 A | 7/1995 | Hooven et al. | |
| 5,441,494 A * | 8/1995 | Ortiz | 606/1 |
| 5,452,836 A | 9/1995 | Huitema et al. | |
| 5,454,378 A | 10/1995 | Palmer et al. | |
| 5,454,827 A | 10/1995 | Aust et al. | |
| 5,465,894 A | 11/1995 | Clark et al. | |
| 5,472,132 A | 12/1995 | Savage et al. | |
| 5,474,566 A | 12/1995 | Alesi et al. | |
| 5,476,206 A | 12/1995 | Green et al. | |
| 5,476,479 A | 12/1995 | Green et al. | |
| 5,478,003 A | 12/1995 | Green et al. | |
| 5,480,089 A | 1/1996 | Blewett | |
| 5,480,409 A | 1/1996 | Riza | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,489,256 A | 2/1996 | Adair | |
| 5,497,933 A | 3/1996 | DeFonzo et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,527,320 A | 6/1996 | Carruthers et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,547,117 A | 8/1996 | Hamblin et al. | |
| 5,549,628 A | 8/1996 | Cooper et al. | |
| 5,553,675 A | 9/1996 | Pitzen et al. | |
| 5,554,169 A | 9/1996 | Green et al. | |
| 5,558,665 A | 9/1996 | Kieturakis | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,564,615 A | 10/1996 | Bishop et al. | |
| 5,571,116 A | 11/1996 | Bolanos et al. | |
| 5,574,431 A | 11/1996 | McKeown et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,978 A | 12/1996 | Green et al. | |
| 5,580,067 A | 12/1996 | Hamblin et al. | |
| 5,582,611 A | 12/1996 | Tsuruta et al. | |
| 5,582,617 A | 12/1996 | Klieman et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,591,170 A | 1/1997 | Spievack et al. | |
| 5,597,107 A | 1/1997 | Knodel et al. | |
| 5,599,151 A | 2/1997 | Daum et al. | |
| 5,601,224 A | 2/1997 | Bishop et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,618,294 A | 4/1997 | Aust et al. | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,782 A | 5/1997 | Adair | |
| 5,632,432 A | 5/1997 | Schulze et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,643,291 A | 7/1997 | Pier et al. | |
| 5,645,209 A | 7/1997 | Green et al. | |
| 5,647,526 A | 7/1997 | Green et al. | |
| 5,651,491 A | 7/1997 | Heaton et al. | |
| 5,653,374 A | 8/1997 | Young et al. | |
| 5,657,921 A | 8/1997 | Young et al. | |
| 5,658,300 A | 8/1997 | Bito et al. | |
| 5,662,258 A | 9/1997 | Knodel et al. | |
| 5,662,662 A | 9/1997 | Bishop et al. | |
| 5,667,517 A | 9/1997 | Hooven | |
| 5,669,544 A | 9/1997 | Schulze et al. | |
| 5,669,918 A | 9/1997 | Balazs et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,685,474 A | 11/1997 | Seeber | |
| 5,688,270 A | 11/1997 | Yates et al. | |

(56) References Cited

U.S. PATENT DOCUMENTS

| | | |
|---|---|---|
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,700,270 A | 12/1997 | Peyser et al. |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,772,578 A | 6/1998 | Heimberger et al. |
| 5,779,130 A | 7/1998 | Alesi et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,809,441 A | 9/1998 | McKee |
| 5,810,811 A | 9/1998 | Yates et al. |
| 5,813,813 A * | 9/1998 | Daum et al. ............ 414/7 |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,690 A | 11/1998 | Yates et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,855,311 A | 1/1999 | Hamblin et al. |
| 5,865,361 A | 2/1999 | Milliman et al. |
| 5,871,135 A | 2/1999 | Williamson, IV et al. |
| 5,873,885 A | 2/1999 | Weidenbenner |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,899,914 A | 5/1999 | Zirps et al. |
| 5,901,895 A | 5/1999 | Heaton et al. |
| 5,906,625 A | 5/1999 | Bito et al. |
| 5,911,353 A | 6/1999 | Bolanos et al. |
| 5,915,616 A | 6/1999 | Viola et al. |
| 5,918,791 A | 7/1999 | Sorrentino et al. |
| 5,931,853 A | 8/1999 | McEwen et al. |
| 5,938,667 A | 8/1999 | Peyser et al. |
| 5,941,442 A | 8/1999 | Geiste et al. |
| 5,951,552 A | 9/1999 | Long et al. |
| 5,951,574 A | 9/1999 | Stefanchik et al. |
| 5,954,259 A | 9/1999 | Viola et al. |
| 5,988,479 A | 11/1999 | Palmer |
| 6,010,054 A | 1/2000 | Johnson et al. |
| 6,012,494 A | 1/2000 | Balazs |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,032,849 A | 3/2000 | Mastri et al. |
| 6,033,378 A | 3/2000 | Lundquist et al. |
| 6,071,233 A | 6/2000 | Ishikawa et al. |
| 6,079,606 A | 6/2000 | Milliman et al. |
| 6,082,577 A | 7/2000 | Coates et al. |
| 6,083,234 A | 7/2000 | Nicholas et al. |
| 6,086,600 A | 7/2000 | Kortenbach |
| 6,099,537 A | 8/2000 | Sugai et al. |
| 6,102,271 A | 8/2000 | Longo et al. |
| 6,109,500 A | 8/2000 | Alli et al. |
| 6,120,433 A | 9/2000 | Mizuno et al. |
| 6,126,670 A | 10/2000 | Walker et al. |
| 6,131,789 A | 10/2000 | Schulze et al. |
| 6,155,473 A | 12/2000 | Tompkins et al. |
| 6,156,056 A | 12/2000 | Kearns et al. |
| 6,159,146 A | 12/2000 | El Gazayerli |
| 6,162,208 A | 12/2000 | Hipps |
| 6,179,776 B1 | 1/2001 | Adams et al. |
| 6,182,673 B1 | 2/2001 | Kindermann et al. |
| 6,202,914 B1 | 3/2001 | Geiste et al. |
| 6,223,835 B1 | 5/2001 | Habedank et al. |
| 6,241,139 B1 | 6/2001 | Milliman et al. |
| 6,249,076 B1 | 6/2001 | Madden et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,309,403 B1 | 10/2001 | Minor et al. |
| 6,315,184 B1 | 11/2001 | Whitman |
| 6,320,123 B1 | 11/2001 | Reimers |
| 6,325,810 B1 | 12/2001 | Hamilton et al. |
| 6,330,965 B1 | 12/2001 | Milliman et al. |
| 6,352,503 B1 | 3/2002 | Matsui et al. |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,492,785 B1 | 12/2002 | Kasten et al. |
| 6,503,257 B2 | 1/2003 | Grant et al. |
| 6,505,768 B2 | 1/2003 | Whitman |
| 6,511,468 B1 | 1/2003 | Cragg et al. |
| 6,522,101 B2 | 2/2003 | Malackowski |
| 6,550,546 B2 | 4/2003 | Thurler et al. |
| 6,569,085 B2 | 5/2003 | Kortenbach et al. |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,641,528 B2 | 11/2003 | Torii |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,705,503 B1 | 3/2004 | Pedicini et al. |
| 6,716,232 B1 | 4/2004 | Vidal et al. |
| 6,716,233 B1 | 4/2004 | Whitman |
| 6,740,030 B2 | 5/2004 | Martone et al. |
| 6,749,560 B1 | 6/2004 | Konstorum et al. |
| 6,752,816 B2 | 6/2004 | Culp et al. |
| 6,755,338 B2 | 6/2004 | Hahnen et al. |
| 6,761,685 B2 | 7/2004 | Adams et al. |
| 6,773,438 B1 | 8/2004 | Knodel et al. |
| 6,786,382 B1 | 9/2004 | Hoffman |
| 6,786,864 B2 | 9/2004 | Matsuura et al. |
| 6,790,173 B2 | 9/2004 | Saadat et al. |

(56) References Cited

U.S. PATENT DOCUMENTS

| | | |
|---|---|---|
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,878,106 B1 | 4/2005 | Herrmann et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,984,203 B2 | 1/2006 | Tartaglia et al. |
| 6,986,451 B1 | 1/2006 | Mastri et al. |
| 6,988,649 B2 | 1/2006 | Shelton, IV et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,029,435 B2 | 4/2006 | Nakao |
| 7,032,798 B2 | 4/2006 | Whitman et al. |
| 7,036,680 B1 | 5/2006 | Flannery |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,059,508 B2 | 6/2006 | Shelton, IV et al. |
| 7,066,944 B2 | 6/2006 | Laufer et al. |
| 7,070,559 B2 | 7/2006 | Adams et al. |
| 7,077,856 B2 | 7/2006 | Whitman |
| 7,083,075 B2 | 8/2006 | Swayze et al. |
| 7,090,637 B2 | 8/2006 | Danitz et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,098,794 B2 | 8/2006 | Lindsay et al. |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,650 B2* | 12/2006 | Lee ................ 606/205 |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,338,513 B2* | 3/2008 | Lee et al. ................ 606/205 |
| 7,494,499 B2* | 2/2009 | Nagase et al. ............ 606/205 |
| 7,575,144 B2 | 8/2009 | Ortiz et al. |
| 7,674,255 B2* | 3/2010 | Braun ................ 606/1 |
| 7,686,826 B2 | 3/2010 | Lee et al. |
| 7,815,565 B2 | 10/2010 | Stefanchik et al. |
| 8,236,010 B2 | 8/2012 | Ortiz et al. |
| 2002/0049454 A1 | 4/2002 | Whitman et al. |
| 2002/0095175 A1 | 7/2002 | Brock et al. |
| 2002/0117534 A1 | 8/2002 | Green et al. |
| 2002/0143078 A1 | 10/2002 | Awokola et al. |
| 2002/0143346 A1 | 10/2002 | McGuckin et al. |
| 2002/0165541 A1 | 11/2002 | Whitman |
| 2003/0023142 A1 | 1/2003 | Grabover et al. |
| 2003/0036748 A1 | 2/2003 | Cooper et al. |
| 2003/0065358 A1 | 4/2003 | Frecker et al. |
| 2003/0105478 A1 | 6/2003 | Whitman et al. |
| 2003/0130677 A1 | 7/2003 | Whitman et al. |
| 2003/0195387 A1 | 10/2003 | Kortenbach et al. |
| 2003/0216778 A1 | 11/2003 | Weadock |
| 2003/0233066 A1* | 12/2003 | Ewers et al. ................ 604/27 |
| 2004/0028502 A1 | 2/2004 | Cummins |
| 2004/0068161 A1 | 4/2004 | Couvillon |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0108357 A1 | 6/2004 | Milliman et al. |
| 2004/0111081 A1 | 6/2004 | Whitman et al. |
| 2004/0116952 A1 | 6/2004 | Sakurai et al. |
| 2004/0122471 A1 | 6/2004 | Toby et al. |
| 2004/0133075 A1 | 7/2004 | Motoki et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0193007 A1 | 9/2004 | Martone et al. |
| 2004/0193146 A1 | 9/2004 | Lee et al. |
| 2004/0222268 A1 | 11/2004 | Bilotti et al. |
| 2004/0230096 A1 | 11/2004 | Stefanchik et al. |
| 2004/0230097 A1* | 11/2004 | Stefanchik et al. ............ 600/127 |
| 2004/0230214 A1 | 11/2004 | Donofrio et al. |
| 2004/0232195 A1 | 11/2004 | Shelton et al. |
| 2004/0232196 A1 | 11/2004 | Shelton et al. |
| 2004/0232199 A1 | 11/2004 | Shelton et al. |
| 2004/0232201 A1 | 11/2004 | Wenchell et al. |
| 2004/0236316 A1 | 11/2004 | Danitz et al. |
| 2004/0243151 A1 | 12/2004 | Demmy et al. |
| 2004/0243176 A1 | 12/2004 | Hahnen et al. |
| 2005/0006429 A1 | 1/2005 | Wales et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0033357 A1 | 2/2005 | Braun |
| 2005/0070885 A1 | 3/2005 | Nobis et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0085693 A1 | 4/2005 | Belson et al. |
| 2005/0096694 A1 | 5/2005 | Lee |
| 2005/0103819 A1 | 5/2005 | Racenet et al. |
| 2005/0107824 A1 | 5/2005 | Hillstead et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131163 A1 | 6/2005 | Rhine et al. |
| 2005/0131164 A1 | 6/2005 | Lenges et al. |
| 2005/0131173 A1 | 6/2005 | McDaniel et al. |
| 2005/0131211 A1 | 6/2005 | Bayley et al. |
| 2005/0131212 A1 | 6/2005 | Sieg et al. |
| 2005/0131279 A1 | 6/2005 | Boulais et al. |
| 2005/0131390 A1 | 6/2005 | Heinrich et al. |
| 2005/0137423 A1 | 6/2005 | Oikawa et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145671 A1 | 7/2005 | Viola |
| 2005/0149067 A1 | 7/2005 | Takemoto et al. |
| 2005/0152416 A1 | 7/2005 | Chang |
| 2005/0154258 A1 | 7/2005 | Tartaglia et al. |
| 2005/0165415 A1 | 7/2005 | Wales |
| 2005/0165419 A1 | 7/2005 | Sauer et al. |
| 2005/0171522 A1 | 8/2005 | Christopherson |
| 2005/0173490 A1 | 8/2005 | Shelton |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187576 A1 | 8/2005 | Whitman et al. |

(56) References Cited

U.S. PATENT DOCUMENTS

| | | |
|---|---|---|
| 2005/0189397 A1 | 9/2005 | Jankowski |
| 2005/0192609 A1 | 9/2005 | Whitman et al. |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0230453 A1 | 10/2005 | Viola |
| 2005/0234297 A1 | 10/2005 | Devierre et al. |
| 2005/0256452 A1 | 11/2005 | DeMarchi et al. |
| 2005/0263562 A1 | 12/2005 | Shelton et al. |
| 2005/0263563 A1 | 12/2005 | Racenet et al. |
| 2005/0273084 A1* | 12/2005 | Hinman et al. ............ 606/1 |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020287 A1* | 1/2006 | Lee et al. ............ 606/205 |
| 2006/0025811 A1 | 2/2006 | Shelton |
| 2006/0025812 A1 | 2/2006 | Shelton |
| 2006/0025813 A1 | 2/2006 | Shelton et al. |
| 2006/0025816 A1 | 2/2006 | Shelton |
| 2006/0041188 A1 | 2/2006 | Dirusso et al. |
| 2006/0047303 A1 | 3/2006 | Ortiz et al. |
| 2006/0047308 A1 | 3/2006 | Ortiz et al. |
| 2006/0049229 A1 | 3/2006 | Milliman et al. |
| 2006/0060630 A1 | 3/2006 | Shelton et al. |
| 2006/0079735 A1 | 4/2006 | Martone et al. |
| 2006/0087442 A1 | 4/2006 | Smith et al. |
| 2006/0094931 A1 | 5/2006 | Danitz et al. |
| 2006/0097026 A1 | 5/2006 | Shelton |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0190029 A1 | 8/2006 | Wales |
| 2006/0190031 A1 | 8/2006 | Wales et al. |
| 2006/0226196 A1 | 10/2006 | Hueil et al. |
| 2006/0229665 A1 | 10/2006 | Wales et al. |
| 2006/0258904 A1 | 11/2006 | Stefanchik et al. |
| 2006/0258907 A1 | 11/2006 | Stefanchik et al. |
| 2006/0273084 A1 | 12/2006 | Baker et al. |
| 2006/0278681 A1 | 12/2006 | Viola et al. |
| 2006/0278880 A1 | 12/2006 | Lee et al. |
| 2006/0289602 A1 | 12/2006 | Wales et al. |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton |
| 2007/0073340 A1 | 3/2007 | Shelton et al. |
| 2007/0075114 A1 | 4/2007 | Shelton et al. |
| 2007/0083234 A1 | 4/2007 | Shelton et al. |
| 2007/0084897 A1 | 4/2007 | Shelton et al. |
| 2007/0088340 A1 | 4/2007 | Brock et al. |
| 2007/0102452 A1 | 5/2007 | Shelton et al. |
| 2007/0102453 A1 | 5/2007 | Morgan et al. |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0102476 A1 | 5/2007 | Shelton et al. |
| 2007/0106113 A1 | 5/2007 | Ravo |
| 2007/0106317 A1 | 5/2007 | Shelton et al. |
| 2007/0129605 A1 | 6/2007 | Schaaf |
| 2007/0158358 A1 | 7/2007 | Mason et al. |
| 2007/0170225 A1 | 7/2007 | Shelton et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175962 A1 | 8/2007 | Shelton et al. |
| 2007/0175964 A1 | 8/2007 | Shelton et al. |
| 2007/0179476 A1 | 8/2007 | Shelton et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221701 A1 | 9/2007 | Ortiz et al. |
| 2007/0225562 A1 | 9/2007 | Spivey et al. |
| 2007/0225694 A1 | 9/2007 | Stefanchik et al. |
| 2007/0233053 A1 | 10/2007 | Shelton et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0065116 A1 | 3/2008 | Lee et al. |
| 2008/0078802 A1 | 4/2008 | Hess et al. |
| 2008/0082124 A1 | 4/2008 | Hess et al. |
| 2010/0331856 A1 | 12/2010 | Carlson et al. |
| 2011/0144430 A1 | 6/2011 | Spivey et al. |
| 2011/0163146 A1 | 7/2011 | Ortiz et al. |
| 2011/0295242 A1 | 12/2011 | Spivey et al. |
| 2012/0199632 A1 | 8/2012 | Spivey et al. |
| 2012/0283748 A1 | 11/2012 | Ortiz et al. |
| 2013/0012931 A1 | 1/2013 | Spivey et al. |
| 2013/0197556 A1 | 8/2013 | Shelton, IV et al. |

FOREIGN PATENT DOCUMENTS

| | | |
|---|---|---|
| CA | 2514274 A1 | 1/2006 |
| DE | 19509116 A1 | 9/1996 |
| DE | 10052679 A1 | 5/2001 |
| DE | 20112837 | 10/2001 |
| DE | 10314072 A1 | 10/2004 |
| DE | 69328576 C5 | 8/2008 |
| EP | 0033548 A2 | 8/1981 |
| EP | 0122046 A1 | 10/1984 |
| EP | 0392547 A1 | 10/1990 |
| EP | 0484677 A1 | 5/1992 |
| EP | 0537572 A2 | 4/1993 |
| EP | 0541987 A1 | 5/1993 |
| EP | 0 552 050 | 7/1993 |
| EP | 0 552 423 | 7/1993 |
| EP | 0592244 A2 | 4/1994 |
| EP | 0593920 A1 | 4/1994 |
| EP | 0598618 | 5/1994 |
| EP | 0600182 A | 6/1994 |
| EP | 0603472 A2 | 6/1994 |
| EP | 0625335 A1 | 11/1994 |
| EP | 0630612 A1 | 12/1994 |
| EP | 0 634 144 | 1/1995 |
| EP | 0634144 A1 | 1/1995 |
| EP | 0639349 A2 | 2/1995 |
| EP | 0 646 356 | 4/1995 |
| EP | 0646357 A1 | 4/1995 |
| EP | 0648476 A1 | 4/1995 |
| EP | 0656188 A2 | 6/1995 |
| EP | 0667119 A1 | 8/1995 |
| EP | 0669104 A1 | 8/1995 |
| EP | 0679367 A2 | 11/1995 |
| EP | 0685204 A1 | 12/1995 |
| EP | 0699418 A1 | 3/1996 |
| EP | 0702937 A1 | 3/1996 |
| EP | 0 705 570 | 4/1996 |
| EP | 0705570 A1 | 4/1996 |
| EP | 0705571 A1 | 4/1996 |

(56) References Cited

FOREIGN PATENT DOCUMENTS

| | | |
|---|---|---|
| EP | 0760230 A1 | 3/1997 |
| EP | 0770355 A1 | 5/1997 |
| EP | 0813843 A1 | 12/1997 |
| EP | 0829235 A1 | 3/1998 |
| EP | 0872213 A2 | 10/1998 |
| EP | 0878169 A1 | 11/1998 |
| EP | 0 880 338 | 12/1998 |
| EP | 0888749 A1 | 1/1999 |
| EP | 0908152 A1 | 4/1999 |
| EP | 0 552 050 B1 | 10/2000 |
| EP | 1045672 A1 | 10/2000 |
| EP | 1064883 A1 | 1/2001 |
| EP | 1086713 A2 | 3/2001 |
| EP | 1090592 A1 | 4/2001 |
| EP | 1129665 A1 | 9/2001 |
| EP | 1238634 A2 | 9/2002 |
| EP | 1256317 A2 | 11/2002 |
| EP | 1256318 A1 | 11/2002 |
| EP | 1 284 120 | 2/2003 |
| EP | 1300117 A2 | 4/2003 |
| EP | 1382303 A1 | 1/2004 |
| EP | 1 400 214 | 3/2004 |
| EP | 1 402 837 | 3/2004 |
| EP | 1 426 012 | 6/2004 |
| EP | 1426012 A1 | 6/2004 |
| EP | 1442694 A1 | 8/2004 |
| EP | 1 459 695 | 9/2004 |
| EP | 1477119 A1 | 11/2004 |
| EP | 1479345 A1 | 11/2004 |
| EP | 1 535 565 | 6/2005 |
| EP | 1 566 150 | 8/2005 |
| EP | 1 593 337 | 11/2005 |
| EP | 1 607 050 | 12/2005 |
| EP | 2 005 896 A2 | 12/2008 |
| GB | 2109241 | 6/1983 |
| GB | 2272159 | 5/1994 |
| GB | 2 284 242 | 5/1995 |
| JP | 7-255735 A | 10/1995 |
| JP | 8-164141 A | 6/1996 |
| JP | 2000033071 | 2/2000 |
| JP | 2000171730 | 6/2000 |
| JP | 2000325303 | 11/2000 |
| JP | 2002143078 | 5/2002 |
| JP | 2003-135473 A | 5/2003 |
| JP | 2003-252639 A | 9/2003 |
| JP | 2004-329624 A | 11/2004 |
| JP | 2005131163 | 5/2005 |
| JP | 2005131164 | 5/2005 |
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| JP | 2005-328882 A | 12/2005 |
| WO | 9314690 A1 | 8/1993 |
| WO | WO-94/11057 | 5/1994 |
| WO | WO-00/48506 | 8/2000 |
| WO | WO-00/54653 | 9/2000 |
| WO | WO-00/72762 | 12/2000 |
| WO | WO-00/72765 | 12/2000 |
| WO | 0162161 A1 | 8/2001 |
| WO | WO-02/43571 | 6/2002 |
| WO | WO-03/000138 | 1/2003 |
| WO | WO-03/015604 | 2/2003 |
| WO | WO-03013363 A1 | 2/2003 |
| WO | WO-03020106 A2 | 3/2003 |
| WO | WO-03030743 A2 | 4/2003 |
| WO | WO-03037193 A1 | 5/2003 |
| WO | WO-03047436 A2 | 6/2003 |
| WO | WO-03057048 A1 | 7/2003 |
| WO | WO-03057058 A1 | 7/2003 |
| WO | WO-03063694 A1 | 8/2003 |
| WO | WO-03/077769 | 9/2003 |
| WO | WO-03077769 A1 | 9/2003 |
| WO | WO-03079909 A2 | 10/2003 |
| WO | WO-03082126 A1 | 10/2003 |
| WO | WO-03088845 A2 | 10/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105702 A2 | 12/2003 |
| WO | WO-2004006980 A2 | 1/2004 |
| WO | WO-2004/019769 | 3/2004 |
| WO | WO-2004/021868 | 3/2004 |
| WO | WO-2004019769 A1 | 3/2004 |
| WO | WO-2004021868 A2 | 3/2004 |
| WO | WO-2004/034875 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004034875 A2 | 4/2004 |
| WO | WO-2004/047626 | 6/2004 |
| WO | WO-2004/052426 | 6/2004 |
| WO | WO-2004047626 A1 | 6/2004 |
| WO | WO-2004047653 A2 | 6/2004 |
| WO | WO-2004049956 A2 | 6/2004 |
| WO | WO-2004052426 A2 | 6/2004 |
| WO | WO-2004086987 A1 | 10/2004 |
| WO | WO-2004/096015 | 11/2004 |
| WO | WO-2004096015 A2 | 11/2004 |
| WO | WO-2004096057 A2 | 11/2004 |
| WO | WO-2004/103157 | 12/2004 |
| WO | WO-2004/105593 | 12/2004 |
| WO | WO-2004103157 A2 | 12/2004 |
| WO | WO-2004105593 A1 | 12/2004 |
| WO | WO-2004112618 A2 | 12/2004 |
| WO | WO-2005027983 A2 | 3/2005 |
| WO | WO-2005044078 A2 | 5/2005 |
| WO | WO-2005096954 A2 | 10/2005 |
| WO | WO-2005115251 A1 | 12/2005 |
| WO | WO-2006044490 A2 | 4/2006 |
| WO | WO-2006044581 A2 | 4/2006 |
| WO | WO-2006044810 A2 | 4/2006 |
| WO | WO-2006083748 A1 | 8/2006 |
| WO | WO-2006132992 A2 | 12/2006 |
| WO | WO-2007016290 A2 | 2/2007 |
| WO | 2007/146987 A2 | 12/2007 |
| WO | 2008/101228 A2 | 8/2008 |
| WO | 2010/050771 A2 | 5/2010 |

OTHER PUBLICATIONS

European Search Report, Application No. 07251221.3, Issued Apr. 23, 2009, 10 pages.

Frederick Van Meer, et al., "A Disposable Plastic Compact Wrist for Smart Minimally Invasive Surgical Tools," LAAS/CNRS (Aug. 2005).

Disclosed Anonymously 'Motor-Driven Surgical Stapler Improvements' Research Disclosure Database No. 526041, Published: Feb. 2008.

European Search Report, Application No. 07250393.1 dated Aug. 9, 2007 (8 pages).

European Search Report issued Dec. 29, 2008 for Application No. 07251221.3 (6 Pages).

International Search Report mailed Jun. 5, 2012 for Application No. PCT/US2012/026985 (6 Pages).

Japanese Office Action issued Mar. 6, 2012 for Application No. 2007-075123 (4 Pages).

Japanese Office Action issued Jan. 8, 2013 for Application No. 2007-075139 (2 pages).

International Search Report and Written Opinion mailed Oct. 12, 2012 for Application No. PCT/US2012/039290 (25 Pages).

Japanese Office Action issued Aug. 28, 2012 for Application No. 2007-075136. 2 pages.

* cited by examiner

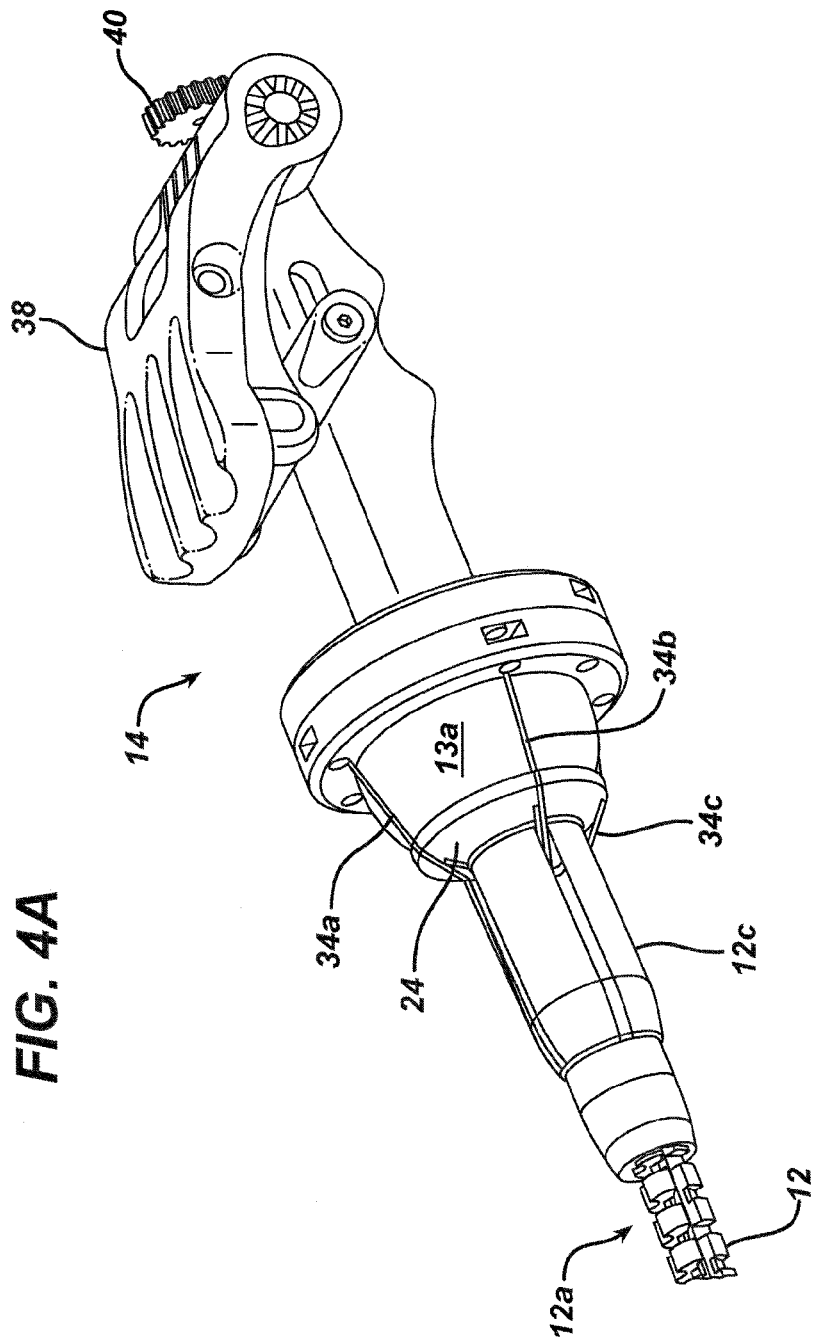

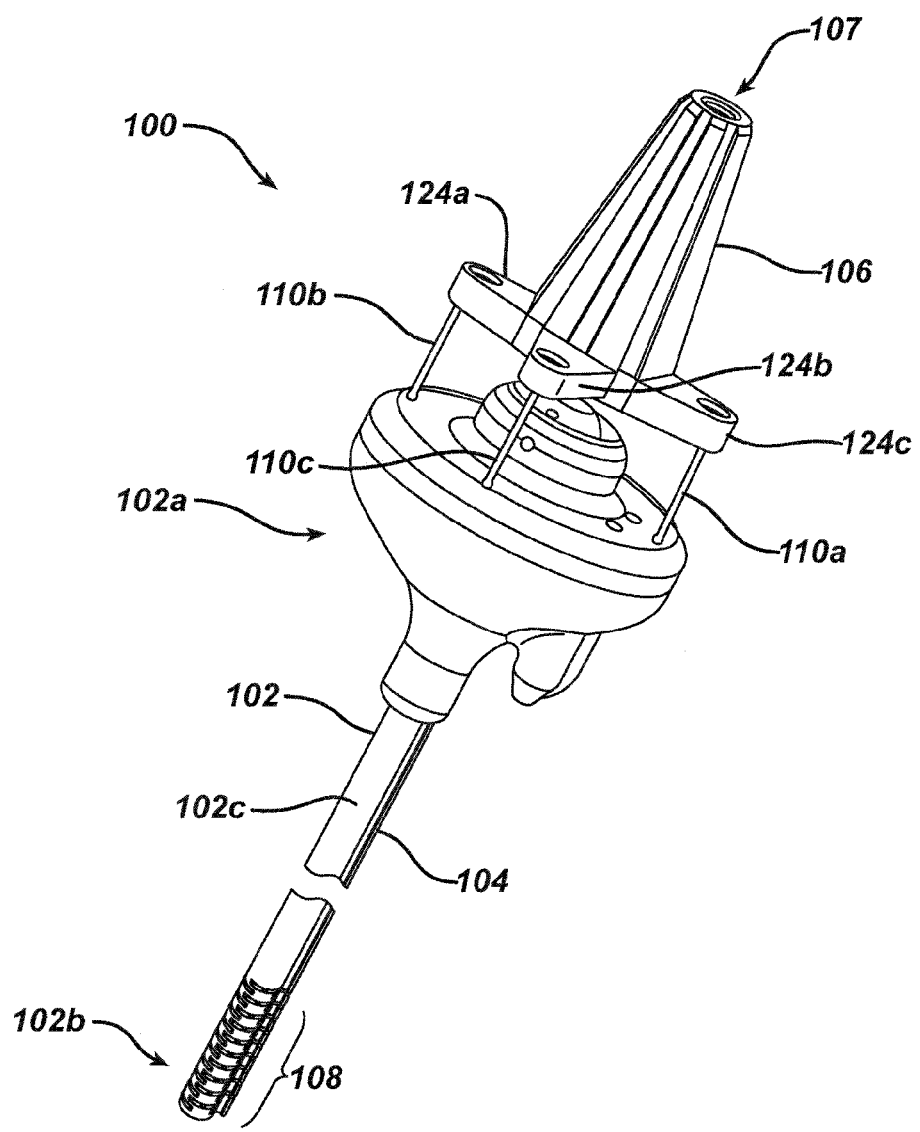

METHODS AND DEVICES FOR CONTROLLING ARTICULATION

FIELD OF THE INVENTION

The present invention relates broadly to methods and devices for controlling movement of a working end of a surgical device.

BACKGROUND OF THE INVENTION

Endoscopic surgical instruments are often preferred over traditional open surgical devices since the use of a natural orifice tends to reduce the post-operative recovery time and complications. Consequently, significant development has gone into a range of endoscopic surgical instruments that are suitable for precise placement of a working end of a tool at a desired surgical site through a natural orifice. These tools can be used to engage and/or treat tissue in a number of ways to achieve a diagnostic or therapeutic effect.

Endoscopic surgery requires that the shaft of the device be flexible while still allowing the working end to be articulated to angularly orient the working end relative to the tissue, and in some cases to be actuated to fire or otherwise effect movement of the working end. Integration of the controls for articulating and actuating a working end of an endoscopic device tend to be complicated by the use of a flexible shaft and by the size constraints of an endoscopic instrument. Generally, the control motions are all transferred through the shaft as longitudinal translations, which can interfere with the flexibility of the shaft. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices.

Accordingly, there remains a need for improved methods and devices for controlling movement of a working end of an endoscopic surgical device.

SUMMARY OF THE INVENTION

In one embodiment, a surgical device is provided having an elongate shaft with a proximal end having a handle movably coupled thereto, and a distal end having a flexible neck extending therefrom. The handle and the flexible neck can be operatively associated such that movement of the handle is effective to cause the flexible neck to articulate in multiple planes. In certain exemplary embodiments, movement of the handle can be mimicked by the flexible neck. The device can also include an actuator extending between the handle and the flexible neck and configured to transfer movement from the handle to the flexible neck.

The handle of the device can have a variety of configurations, but in one embodiment the handle can be adapted to articulate relative to the proximal end of the elongate shaft. For example, the handle can be coupled to the proximal end of the elongate shaft by a joint, such as a ball and socket joint, a hinge joint, or a flexing joint. The actuator of the device can also have a variety of configurations, and in one embodiment the actuator can be at least one cable extending along a length of the elongate shaft. For example, the device can include a plurality of cables extending along a length of the shaft and equally spaced apart from one another around a circumference of the actuator. The cables are configured to slide relative to an axis of the elongate shaft and to apply tension to the elongate shaft to cause at least a portion of the elongate shaft to flex and bend. The handle and/or the cables can also optionally include a locking mechanism associated therewith and configured to maintain the handle and/or cables in a fixed position. In an exemplary embodiment, the elongate shaft is configured to passively flex and bend when it is inserted through a tortuous lumen.

The elongate shaft can also have a variety of configurations, but in one embodiment the device can be in the form of a surgical stapler and the elongate shaft can include an end effector coupled to a distal end of the flexible neck and adapted to engage tissue and deliver at least one fastener into the engaged tissue. The handle and the end effector can be coupled such that movement of the handle is mimicked by the end effector. For example, the handle can be coupled to the proximal end of the elongate shaft by a joint, such as a ball and socket joint, a hinge joint, and a flexing joint, and the flexible neck can be formed on or coupled to the end effector to allow the end effector to proportionally mimic movement of the handle. The device can also include an actuator extending between the handle and the end effector and configured to transfer movement from the handle to the flexible neck. The actuator can be, for example, a plurality of cables extending along a length of the elongate shaft. The cables can be equally spaced apart from one another around a circumference of the elongate shaft.

In another embodiment, the device can be in the form of an accessory channel and the elongate shaft can be in the form of a tube having an inner lumen adapted to receive a tool therethrough. The flexible neck extending from the distal end of the elongate tube can be configured to flex to orient a tool extending through the elongate tube. The flexible neck can have a variety of configurations, but in one embodiment it includes a plurality of slits formed therein to facilitate flexion thereof. The slits can be configured to cause the flexible neck to flex into a desired orientation. For example, the flexible neck can include a distal region of slits and a proximal region of slits, and the slits can be configured such that tension applied to the flexible neck will cause the flexible neck to bend at the proximal and distal regions. A handle can be coupled to the proximal end of the elongate tube, and it can operatively associated with the flexible neck such that movement of the handle is mimicked by the flexible neck. The handle can also have a variety of configurations, and in one embodiment the handle can include a stationary member and a movable member adapted to articulate relative to the stationary member. The movable member can be coupled to the stationary member by a joint, such as a ball and socket joint, a hinge joint, and a flexing joint. In use, the accessory channel can be configured to releasably attach to an endoscope. For example, a mating element can be formed on and extend along a length of an external surface thereof for mating to a complementary mating element formed on a sleeve adapted to receive an endoscope. The device can also include an actuator extending between the handle and the flexible neck. The actuator can be configured to transfer movement from the handle to the flexible neck. In certain exemplary embodiments, the actuator is in the form of at least one cable extending along a length of the elongate tube. Where the actuator includes multiple cables, the cables are preferably equally spaced apart from one another around a circumference of the elongate tube. The cables can extend along the elongate tube using various techniques. For example, the elongate tube can include at least one lumen formed in a sidewall thereof and extending along the length thereof, and the cable(s) can be slidably disposed within the lumen(s). The device can also include a locking mechanism positioned to engage at least one of the handle and the cable(s) to lock the handle and the cable(s) in a fixed position.

The present invention also provides an endoscopic system having an elongate sleeve configured to be disposed around an endoscope, and an accessory channel removably matable to the elongate sleeve. The accessory channel can have an inner lumen extending therethrough between proximal and distal ends thereof for receiving a tool, a flexible portion formed on a distal portion thereof and being made flexible by a plurality of slits formed therein, and at least one handle coupled to the proximal end thereof and operatively associated with the flexible portion such that the handle(s) is configured to cause the flexible portion to articulate in at least one plane. The handle(s) can be operatively associated with the flexible portion by at least one cable, and the handle(s) can be configured to axially move the cable(s) relative to the accessory channel to cause the cable(s) to apply tension to the flexible portion of the accessory channel such that the flexible portion articulates in at least one plane. In one embodiment, the device can include a single handle configured to cause the flexible portion to articulate in multiple planes. The single handle can include a stationary member coupled to the proximal end of the accessory channel, and a movable member configured to articulate relative to the stationary member. The single handle and the flexible portion can be operatively associated such that movement of the single handle is mimicked by the flexible portion. In another embodiment, the handle can include a first member configured to cause the flexible portion to articulate in a first plane, and a second member configured to cause the flexible portion to articulate in a second plane. In particular, the handle can include a stationary member coupled to the proximal end of the accessory channel, and the first and second members can be rotatably coupled to the stationary member. The device can further include a first spool coupled to the first member and having at least one cable extending therefrom and coupled to the flexible portion, and a second spool coupled to the second member and having at least one cable extending therefrom and coupled to the flexible portion. The first and second members can be effective to rotate the first and second spools and thereby move the cables axially to cause the flexible portion to articulate.

The surgical devices disclosed herein can also include a variety of other features. For example, the device can include an optical image gathering unit disposed on a distal end of the elongate shaft. The optical image gathering unit can be adapted to acquire images during endoscopic procedures. An image display screen can be disposed on a proximal portion of the device and adapted to communicate with the optical image gathering unit to display the acquired images. In other embodiments, the end effector of the device can include a cartridge removably disposed therein and containing a plurality of staples for stapling tissue and a blade for cutting stapled tissue.

In other aspects, a surgical method is provided and includes inserting an elongate shaft into a body lumen to position a flexible neck coupled to a distal end of the elongate shaft adjacent to tissue to be treated, and moving a handle pivotally coupled to a proximal end of the elongate shaft to cause the flexible neck to mimic the motion of the handle. The flexible neck can mirror movement of the handle, or movement of the flexible neck can directly correspond to movement of the handle. In certain exemplary embodiments, the movement is proportional.

In one exemplary embodiment, an end effector coupled to a distal end of the elongate shaft is positioned adjacent to tissue to be fastened, and a handle pivotally coupled to a proximal end of the elongate shaft is moved to cause the end effector to proportionally mimic the motion of the handle. The end effector can mirror movement of the handle, or movement of the end effector can directly correspond to movement of the handle. In an exemplary embodiment, the handle is pivotally articulated about the proximal end of the elongate shaft to cause the end effector to mimic the motion of the handle. The method can further include engaging tissue between opposed jaws of the end effector, and driving at least one fastener from the end effector into the tissue. Tissue can be engaging by moving a translating member formed on the handle from a first position to a second position to close the opposed jaws, and the fasteners can be fired by rotating a rotatable member formed on the handle to actuate a driver mechanism disposed within the end effector to cause the driver mechanism to drive a plurality of fasteners into the tissue. In another embodiment, prior to moving the translating member from the first position to the second position, the rotatable member can be rotated to rotate the end effector relative to the flexible neck without actuating the driver mechanism.

In yet another aspect, the elongate shaft can be in the form of an accessory channel that is slidably mated to an endoscope disposed within a body cavity to position a distal end of the accessory channel in proximity to a distal end of the endoscope. A tool is inserted through a lumen in the accessory channel such that the tool extends distally beyond the distal end of the accessory channel, and a handle coupled to a proximal end of the accessory channel can be moved to cause a flexible neck on the distal end of the accessory channel to articulate, thereby causing a working end of the tool to be oriented in a desired position. The handle can be moved by pivotally articulating the handle relative to the accessory channel, or alternatively is can be moved by rotating at least one rotatable member on the handle.

BRIEF DESCRIPTION OF THE DRAWINGS

The invention will be more fully understood from the following detailed description taken in conjunction with the accompanying drawings, in which:

FIG. 4A is a perspective view of a proximal portion of the device shown in FIGS. 1A and 1B, showing a handle movably coupled to a proximal end of a shaft of the device;

FIG. 7 is a perspective view of an accessory channel for use with an endoscope;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides method and devices for controlling a working end of an endoscopic surgical device. In general, the endoscopic surgical devices include an elongate shaft having a distal working end with a flexible neck, and a proximal end with a handle for controlling movement of the flexible neck on the distal working end. In certain exemplary embodiments, this can be achieved using, for example, one or more cables that extend between the handle and the flexible neck such that movement of the handle applies a force to one or more of the cables to cause the flexible portion to flex and thereby move the working end of the device. Various other features are also provided to facilitate use of the device.

A person skilled in the art will appreciate that the particular device being controlled, and the particular configuration of the working end, can vary and that the various control techniques described herein can be used on virtually any surgical device in which it is desirable to control movement of the working end.

Figure 1A:
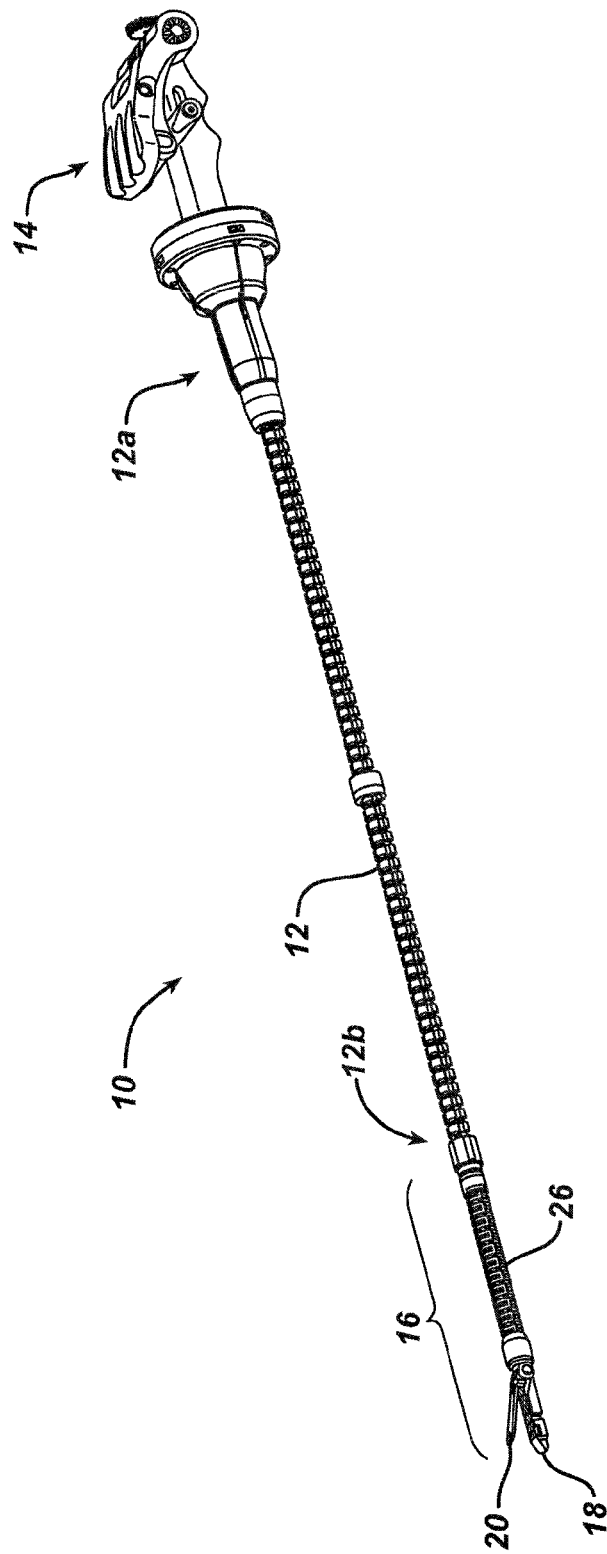
FIG. 1A is a perspective view of one embodiment of a surgical stapling and cutting device, showing a working end of the device in an initial position.
Figure 1B:
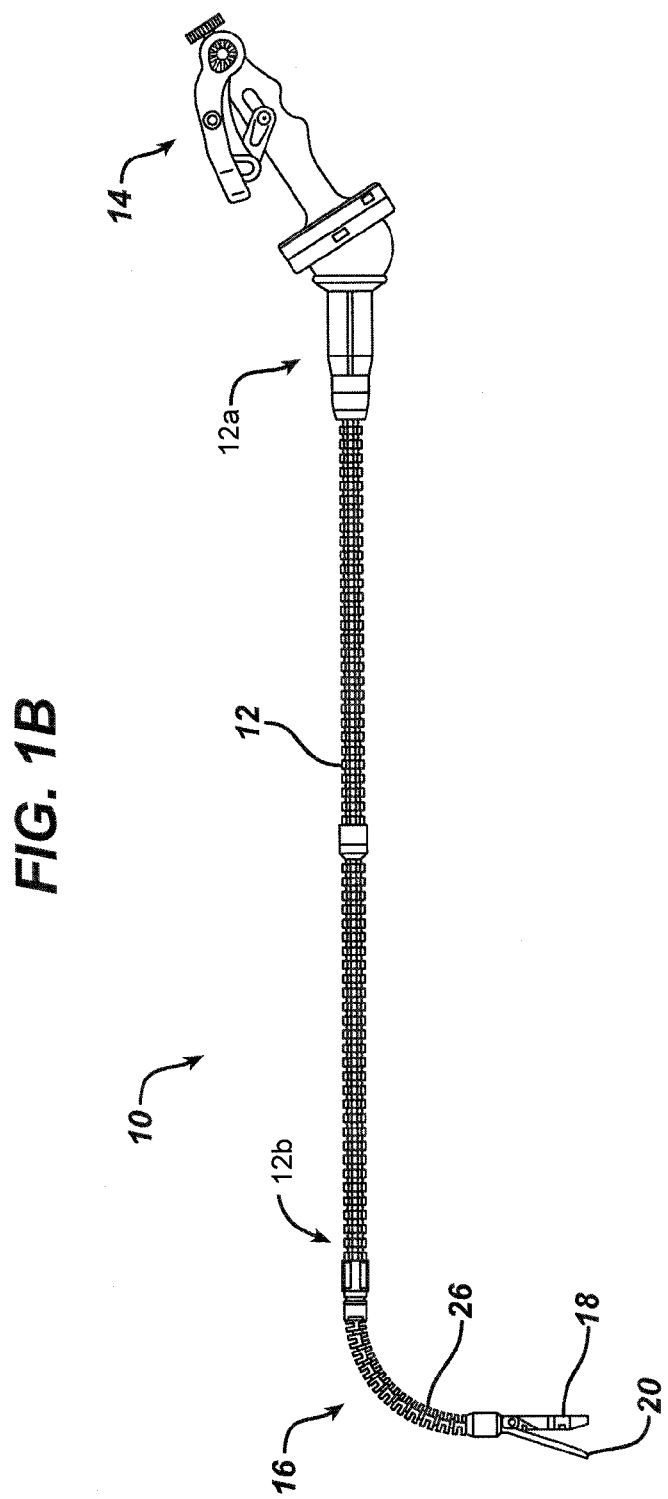
FIG. 1B is a perspective view of the surgical stapling and cutting device of FIG. 1A, showing the working end of the device in an articulated position.

FIGS. 1A and 1B illustrate one exemplary embodiment of a technique for controlling articulation of the end effector, and in particular for causing the end effector to mimic and simultaneously move with the handle. In this embodiment, the device is in the form of a linear stapling and cutting device 10 for applying multiple linear rows of staples to tissue and for cutting the stapled tissue. As shown, the device 10 generally includes an elongate shaft 12 having a proximal end 12a with a handle 14 coupled thereto, and a distal, working end 12b having an end effector 16 coupled thereto or formed thereon, as will be discussed in more detail below. In use, the end effector 16 is configured to mimic movement of the handle 14. Mimicking motion between the handle 14 and the end effector 16 can generally be achieved using an actuator (not shown) that extends between the handle 14 and the end effector 16, and that is effective to transfer forces from the handle 14 to the end effector 16. In an exemplary embodiment, the actuator is in the form of several cables that are spaced around a circumference of the elongate shaft 12, and that extend along the length of the elongate shaft 12. Movement of the handle 14 about the proximal end 12a of the shaft 12 will apply a force to one or more of the cables to cause the cables to apply a force to the end effector 16, thereby causing the end effector 16 to mimic the motion of the handle 14. Mimicking motion can include corresponding motion, whereby the end effector 16 moves in the same direction and orientation as the handle 14, or mirrored motion, whereby the end effector 16 moves in an opposite direction and orientation as the handle 14. The mimicking motion can also be proportional to the movement of the handle.

Figure 2:
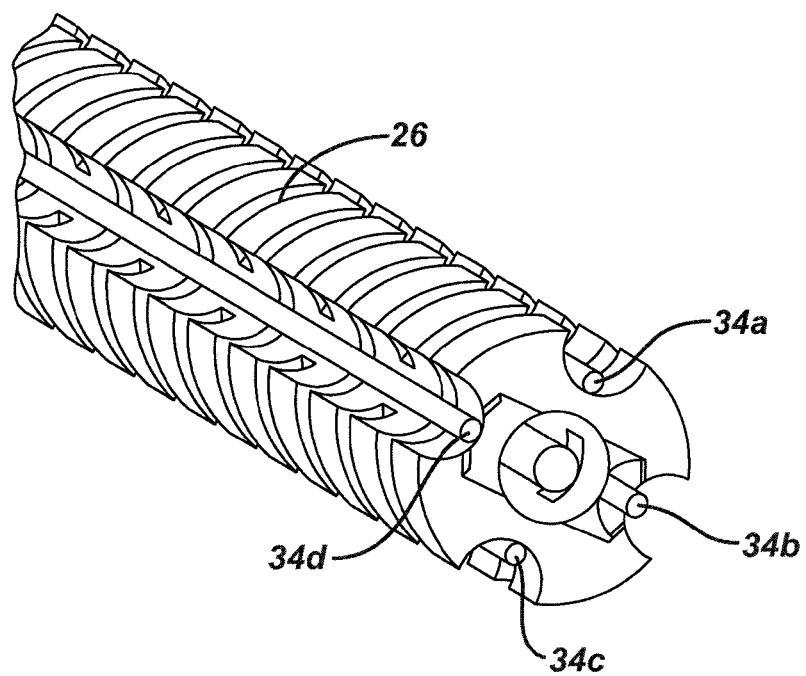
FIG. 2 is a perspective view of a portion of a flexible neck of the device shown in FIGS. 1A and 1B.

The elongate shaft 12 of the device 10 can have a variety of configurations. For example, it can be solid or hollow, and it can be formed from a single component or multiple segments. As shown in FIG. 2, the elongate shaft 12 is hollow and is formed from multiple connecting segments to allow the elongate shaft 12 to flex. The flexibility of the shaft 12, as well as a relatively small diameter, allows the shaft 12 to be used in endoscopic procedures, whereby the device is introduced translumenally through a natural orifice. The shaft can also vary in length depending on the intended application.

FIG. 2 further illustrates one exemplary embodiment of an actuator in the form of several cables 34a, 34b, 34c, 34d that are spaced around a circumference of the elongate shaft 12, and that extend along the length of the elongate shaft 12. The number and location of the cables can vary. For example, three cables can be spaced approximately 120.degree. apart from one another around the circumference of the shaft 12. In the embodiment shown in FIG. 2, four cables 34a, 34b, 34c, 34d are spaced approximately 90.degree. apart from one another around the circumference of the shaft 12. Each cable 34a-d can extend through a pathway, such as a lumen, formed on, in, or around the elongate shaft 12. FIG. 2 illustrates each cable 34a-d extending through a cut-out formed on an external surface of each segment of the shaft 12. Thus, each segment includes four cut-outs spaced equidistant around the circumference of the shaft 12 to maintain the cables 34a-d equidistant from one another. The cut-outs preferably have a size that is effective to retain the cables 34a-d therein while allowing the cables 34a-d to freely slide relative to the shaft 12.

Figure 3A:
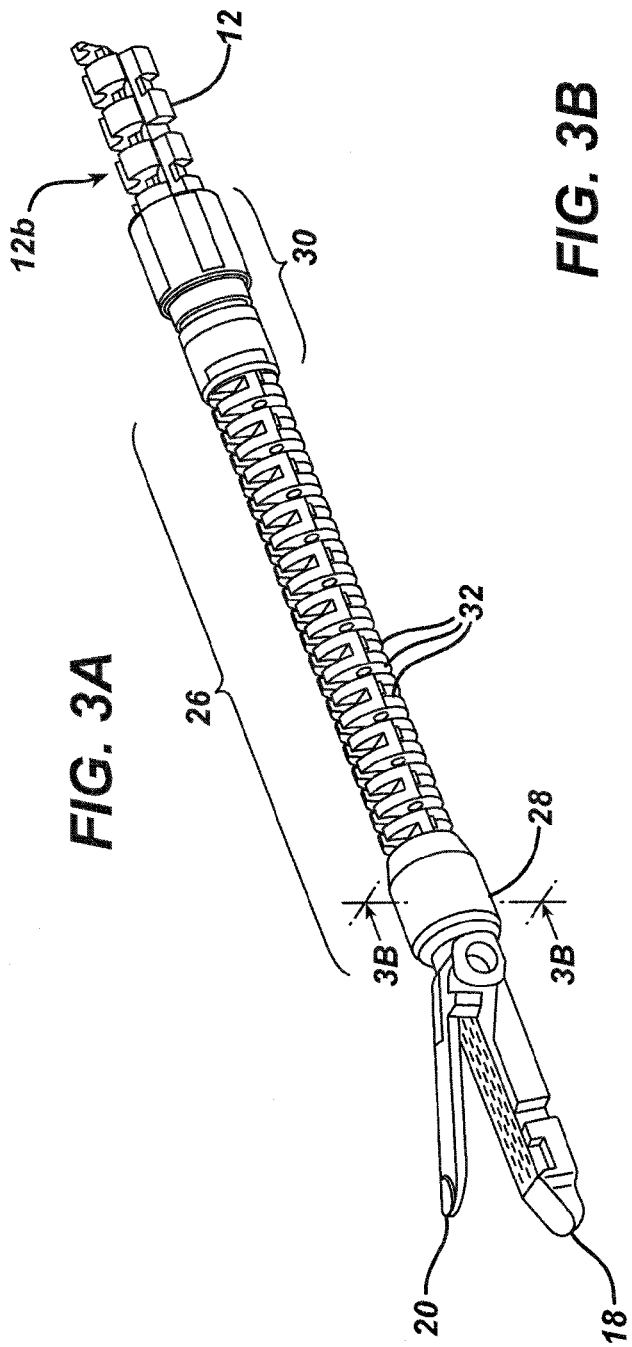
FIG. 3A is a perspective view of a distal portion of the device shown in FIGS. 1A and 1B, showing an end effector and the flexible neck of FIG. 2 coupled thereto.

The distal end of the cables 34*a-d* can be mated to the end effector 16 to control movement of the end effector 16. While the end effector 16 can have a variety of configurations, and various end effectors known in the art can be used, FIG. 3A illustrates one exemplary embodiment of an end effector 16 which generally includes opposed first and second jaws 18, 20 that are adapted to receive tissue therebetween. The first jaw 18 is adapted to contain a staple cartridge having multiple staples disposed therein and configured to be driven into tissue, and the second jaw 20 forms an anvil for deforming the staples. The particular configuration and the basic operation of the end effector 16 can vary, and various end effectors 16 known in the art can be used. By way of non-limiting example, U.S. Pat. No. 6,978,921 entitled "Surgical Stapling Instrument Incorporating an E-Beam Firing Mechanism," which is incorporated herein in its entirety, discloses one embodiment of an end effector that can be used with the present invention.

In order to allow movement of the end effector 16 relative to the elongate shaft 12, the end effector 16 can be movably coupled to the distal end 12*b* of the elongate shaft 12. For example, the end effector 16 can be pivotally coupled to the distal end 12*b* of the elongate shaft 12 by a pivoting or rotating joint. Alternatively, the end effector 16 can include a flexible neck 26 formed thereon, as shown, for allowing movement of the end effector 16 relative to the elongate shaft 12. The flexible neck 26 can be formed integrally with the distal end 12*b* of the shaft 12 and/or the proximal end of the jaws 18, 20, or it can be a separate member that extends between the shaft 12 and the jaws 18, 20. As shown in FIG. 3A, the flexible neck 26 includes a first coupler 28 for mating the flexible neck 26 to the proximal end of the opposed jaws 18, 20, and a second coupler 30 for mating the flexible neck 26 to the distal end of the elongate shaft 12. The couplers 28, 30 can be removably of or fixedly mated to the flexible neck 26 and/or to the jaws 18, 20 and the shaft 12. The couplers 28, 30 also function to house certain components of the end effector 16. For example, the first coupler 28 can function to anchor the cables therein, as will be discussed below, and it can also function to house a gear and driver assembly for actuating (e.g., closing and firing) the jaws 18, 20.

In order to facilitate flexion of the flexible neck 26, the neck 26 can include one or more slits 32 formed therein. The quantity, location, and size of the slits 32 can vary to obtain a desired flexibility. In the embodiment shown in FIG. 3A, the flexible neck 26 includes multiple rows of slits 32, each row extending radially around the flexible neck 26 and each row being spaced axially along the length of the flexible neck 26. Each row of slits contains two slits extending around the circumference of the neck 26, and each row of slits 32 is axially offset from one another. As a result, the flexible neck 26 includes alternating slits 32. A person skilled in the particular pattern of the slits 32 can vary, and that FIG. 3A merely illustrates one pattern for forming slits 32 to allow flexion of the flexible neck 26. Other exemplary slit configurations will be discussed in more detail below.

Figure 3B:
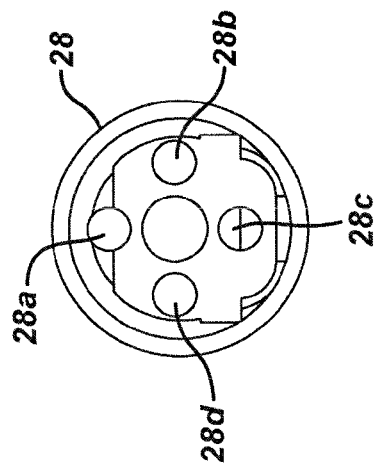
FIG. 3B is a cross-sectional view taken across line 3B-3B of the end effector shown in FIG. 3A.

As indicated above, the cables 34*a-d* can be coupled to the end effector 16 to allow the end effector 16 to move in coordination with the handle 14. The connecting location of the cables 34*a-d* with the end effector 16 can vary depending on the desired movement. In the illustrated embodiment, the distal end of the cables 34*a-d* is connected to the distal end of the flexible neck 26, and in particular they extend into and connect to the first coupler 28. FIG. 3B illustrates a cross-sectional view of the first coupler 28 showing four bores 28*a*, 28*b*, 28*c*, 28*d* for receiving the four cables 34*a*, 34*b*, 34*c*, 34*d*, respectively. Virtually any technique known in the art can be used to connect the cables 34*a-d* to the coupler 28 including, for example, mechanical mating techniques such as adhesives, an interference fit, a ball-and-socket connection, threads, etc. In use, the connection of the cables 34*a-d* at the distal end of the flexible neck 26 will allow the cables 34*a-d* to apply a tension to the flexible neck 26 when an axial force is applied to the cables 34*a-d* by the handle 14. This tension will cause the neck 26 to flex in a direction dictated by the amount of tension applied to each cable 34*a-d*, as will be discussed in more detail below.

Figure 4B:
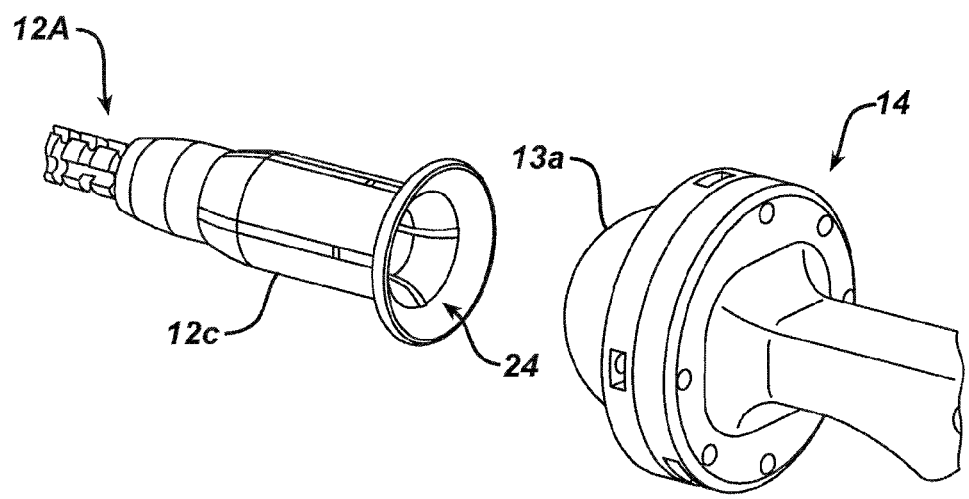
FIG. 4B is an exploded view of the proximal portion of the device shown in FIG. 4A.

The handle 14 of the device 10 can be used to control movement of the end effector 16, and in particular to articulate the end effector 16 and thus angularly orient it relative to a longitudinal axis A of the elongate shaft 12. While the handle 14 can have a variety of configurations, in one exemplary embodiment the handle 14 is movably coupled to the proximal end 12*a* of the elongate shaft 12 such that movement of the handle 14 can be mimicked by the end effector 16. While various techniques can be used to movably couple the handle 14 to the shaft 12, in the embodiment shown in FIGS. 4A-4C, a ball-and-socket connection is formed between the handle 14 and the proximal end 12*a* of the elongate shaft 12. As best shown in FIG. 4B, the proximal end 12*a* of the elongate shaft 12 includes a socket 24 formed therein, and the handle 14 includes a hemi-spherical ball 13*a* formed on a distal end thereof and configured to be rotatably seated within the socket 24. The socket 24 can be integrally formed with the proximal end 12*a* of the elongate shaft, or it can be formed by coupling a hollow housing 12*c*, as shown, to the proximal end 12*a* of the elongate shaft 12. The hemi-spherical ball 13*a* can also be formed integrally with the handle 14, or it can be a separate member that is coupled to the handle 14. In order to movably mate the handle 14 to the shaft 12, the hemi-spherical ball 13*a* on the handle 14 can be retained within the socket 24 using the cables 34*a-d*, which attach to the handle 14 as will be discussed below. However, other mating techniques can be used to movably mate the handle 14 to the shaft 12. For example, the ball 13*a* can be spherical and it can be captured within a spherical socket formed in the proximal end 12*a* of the elongate shaft 12, or a mating element, such as a pin, can extend through the ball 13*a* to retain the ball 13*a* within the socket 24. While FIG. 4B illustrates a ball 13*a* formed on the handle 14 and a socket 24 formed in the shaft 12, the ball-and-socket connection can be reversed such that the ball is on the shaft 12 and the socket is in the handle 14. Moreover, a person skilled in the art will appreciate that a variety of other techniques can be used to movably couple the handle 14 to the proximal end 12*a* of the elongate shaft 12.

In use, the handle 14 can articulate or pivotally move relative to the shaft 12 to cause the end effector 16 to mimic the movement of the handle 14. This can be achieved by coupling the proximal end of the cables 34*a-d* to the handle 14. The connecting location of the cables 34*a-d* with the handle 14 can vary depending on the desired movement. In the illustrated embodiment, the cables (only three cables 34*a*, 34*b* and 34*c* are shown in FIG. 4A) extend from the elongate shaft 12, through the hollow housing 12*c*, and out of slots or openings formed in a proximal end of the hollow housing 12*c*. The cables 34*a-d* then extend around the ball 13*a* on the handle 14 and connect to a distal-facing surface on the handle 14 that surrounds the ball 13*a*. Virtually any technique known in the art can be used to connect the cables 34*a-d* to the handle 14 including, for example, mechanical mating techniques such as adhesives, an interference fit, threads, etc. As shown in FIG. 4A, the handle 14 includes openings formed therein, and the proximal ends (not shown) of the cables 34*a-d* can have a ball or other element formed thereon and configured to be captured within the openings. As further shown in FIG. 4A, the cables (only three cables 34a, 34b and 34c are shown) can remain spaced circumferentially around the handle 14. This will allow movement of the handle 14 to be mirrored by the end effector 16, as will be discussed in more detail below. Alternatively, the cables 34a-d can be crossed before they connect to the handle 14 to cause the end effector 16 to move in the same direction as the handle 14. For example, opposed cables 34a and 34c can cross one another and can connect to opposed sides of the handle 14, and opposed cables 34b and 34d can likewise cross one another and can connect to opposed sides of the handle 14. The cables 34a-d can be crossed at any location, such as within the hollow housing 12c on the proximal end 12a of the shaft 12.

As further shown in FIGS. 4A and 4B, the handle 14 can also include other features to facilitate use of the device. For example, the handle 14 can include a translating member 38 that is effective to close the jaws 18, 20 on the end effector 16, and a rotating member 40 that is effective to selectively rotate and actuate the end effector 16. The translating and rotating members 38, 40 are described in more detail in U.S. application Ser. No. 11/277,320, now U.S. Pat. No. 7,575,144, entitled "Surgical Fastener And Cutter With Single Cable Actuator" by Mark Ortiz et al. and filed on Mar. 23, 2006, which is hereby incorporated by reference in its entirety. In other embodiments, the handle 14 can include triggers, knobs, etc. for rotating and/or actuating the end effector 16.

Referring back to FIG. 1B, in use the handle 14 can be pivoted or angularly oriented relative to the proximal end 12a of the elongate shaft 12 to effect mimicking movement of the end effector 16. In particular, pivoting the handle 14 about the elongate shaft 12 in a first direction will apply a force to one or more of cables 34a-d to pull the cable(s) axially. As a result, the actuated cables will apply tension to the flexible neck 26 to cause the neck 26 to flex. In order to prevent the elongate shaft 12 from flexing in response to tension applied to the cables 34a-d by the handle 14, the flexible neck 26 can have a greater flexibility than the elongate shaft 12. This can be achieved, for example, using the alternating slits 32 as previously described, or in other embodiments the material can differ, or the elongate shaft can include a stabilizing element, such as a rod extending therethrough to render the shaft more rigid than the flexible neck.

The direction of movement of the handle 14 will be mimicked by the end effector 16, either in the same direction (i.e., corresponding movement) or in an opposite direction (i.e., mirrored movement), thus allowing a user to precisely control the position of the end effector 16. In an exemplary embodiment, the particular amount of movement of the end effector 16 can be proportional to the amount of movement of the handle 14. That is, the amount of movement of the end effector 16 can be directly equivalent to the amount of movement of the handle 14, or it can be proportionally increased or decreased relative to the amount of movement of the handle 14. In certain embodiments, it may be desirable to have the amount of movement of the end effector 16 be increased relative to the amount of movement of the handle 14. As a result, only small movements of the handle 14 will be necessary to allow large movements of the end effector 16. While various techniques can be achieved to proportionally multiple or increase the movement of the end effector 16, one exemplary embodiment of a force multiplying mechanism is an eccentric cam that is coupled to the cables and that increases the mechanical advantage, either force or displacement, of the cables 34a-d as tension is applied to the cables 34a-d by the handle 14.

A person skilled in the art will appreciate that, while the movement between the handle and the working end of the device can be proportional in theory, in practice some lose of force will likely occur as the force is transferred through the elongate shaft. Accordingly, proportional movement as used herein is intended to include applications in which the handle and working end are configured to move in proportionate amounts, but in which some lose of force may occur during actual operation of the device.

Figure 5:
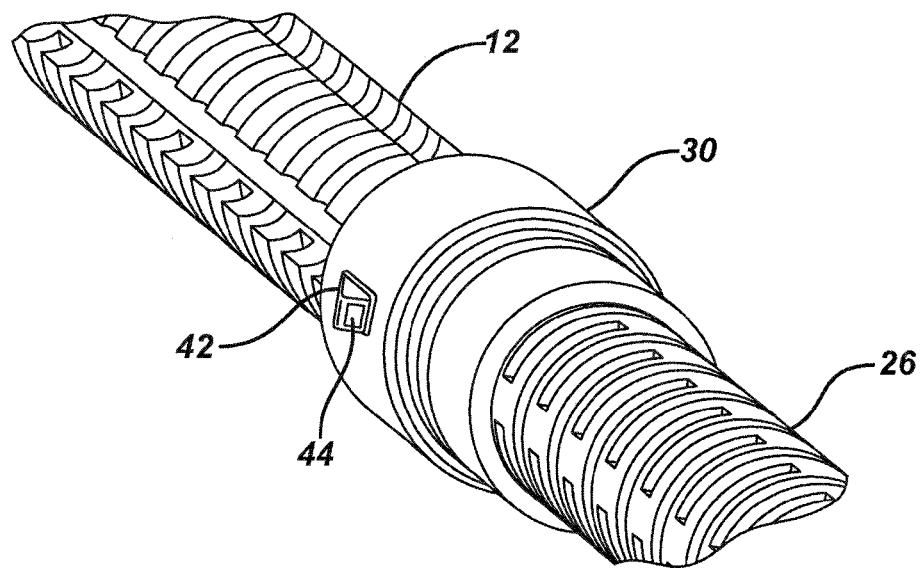
FIG. 5 is a perspective view of coupling element disposed between the flexible neck and elongate shaft of the device shown in FIGS. 1A and 1B, showing an optical image gathering apparatus.
Figure 6:
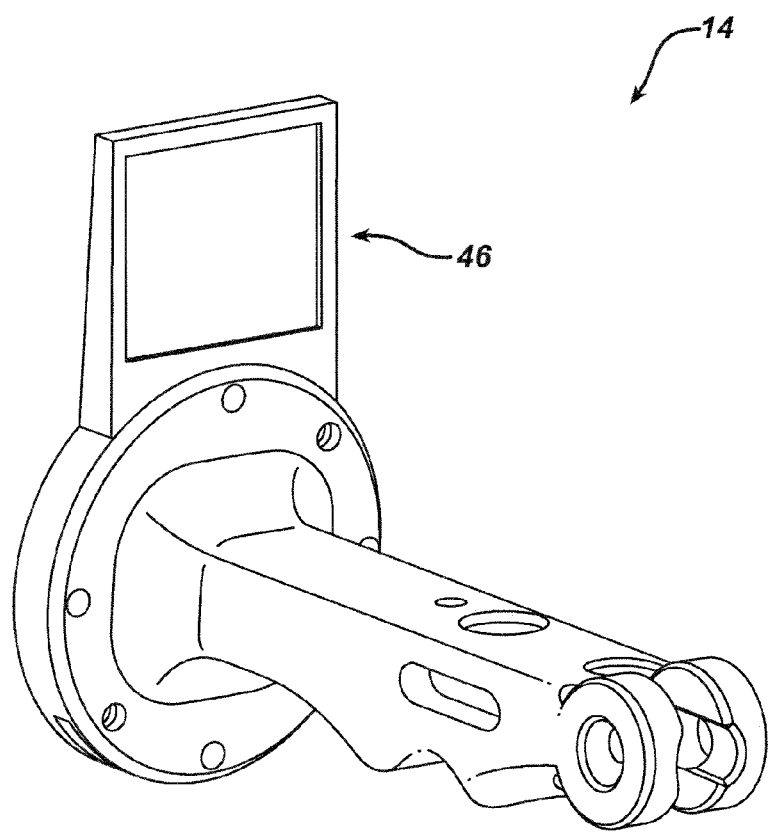
FIG. 6 is a perspective view of the handle of the device shown in FIGS. 1A and 1B, showing an image display screen.

The various devices disclosed herein can also include a variety of other features to facilitate use thereof. For example, the device 10 of FIG. 1A can include an optical image gathering unit disposed on a distal end of the elongate shaft 12 and configured to acquire images during endoscopic procedures. While the location of the unit can vary, in one embodiment the optical image gathering unit can be disposed on the second coupler 30. In particular, FIG. 5 illustrates a ramp-shaped housing 42 that protrudes from an outer surface of the coupler 30, and that contains the optical image gathering unit therein. A viewing window 44 is formed on a distal-facing surface of the housing 42 to allow the unit to acquire images of the end effector 16 and surrounding surgical site. The images from the optical image gathering unit can be transferred to an external image display screen, or alternatively the device 10 can include image display screen disposed on or coupled to a proximal portion of the device. FIG. 6 illustrates one embodiment of an image display screen 46 protruding outward from the handle 14.

As previously indicated, the various techniques disclosed herein for controlling movement of a working end of an endoscopic surgical device can be used in conjunction with a variety of medical devices. FIG. 7 illustrates another embodiment of a medical device having an actuator for controlling movement of the working end thereof. In this embodiment, the medical device is in the form of an accessory channel 100 for use with an endoscope. An accessory channel 100 is an external device that can mate to and slide along an endoscope to allow other tools, such as grasper, cutters, etc., to be introduced therethrough and positioned in proximity to the viewing end of the endoscope. While the accessory channel 100 can have virtually any configuration, shape, and size, in the embodiment illustrated in FIG. 7 the accessory channel 100 includes an elongate tube or shaft 102 having an inner lumen extending between proximal and distal ends 102a, 102b thereof for receiving a tool therethrough. The accessory channel 100 can also include a mating element formed thereon for mating the accessory channel 100 directly to an endoscope or to a sleeve or other device disposed around an endoscope. While virtually any mating technique can be used, in the illustrated embodiment the mating element on the accessory channel 100 is in the form of a rail 104 that extends along a length of the elongate shaft 102. The rail 104 is configured to be received in a complementary track formed on an endoscope or a device disposed around an endoscope, such as a sleeve. A person skilled in the art will appreciate that a variety of other techniques can be used to mate the accessory channel either directly or indirectly to an endoscope.

In order to control movement of a working end of the accessory channel 100, the device 100 can include features similar to those previously described. In particular, the device 100 can a flexible neck 108 formed on or coupled to the distal end 102b of the elongate shaft 102, a handle 106 formed on or coupled to the proximal end 102a of the elongate shaft 102, and an actuator extending between the handle 106 and the flexible neck 108. In this embodiment, the actuator is configured to transfer forces from the handle 106 to the flexible neck 108 such that movement of the handle 106 is mimicked by the flexible neck 108, thus allowing a tool extending through the accessory channel 100 to be positioned at a desired angular orientation.

Figure 8A:
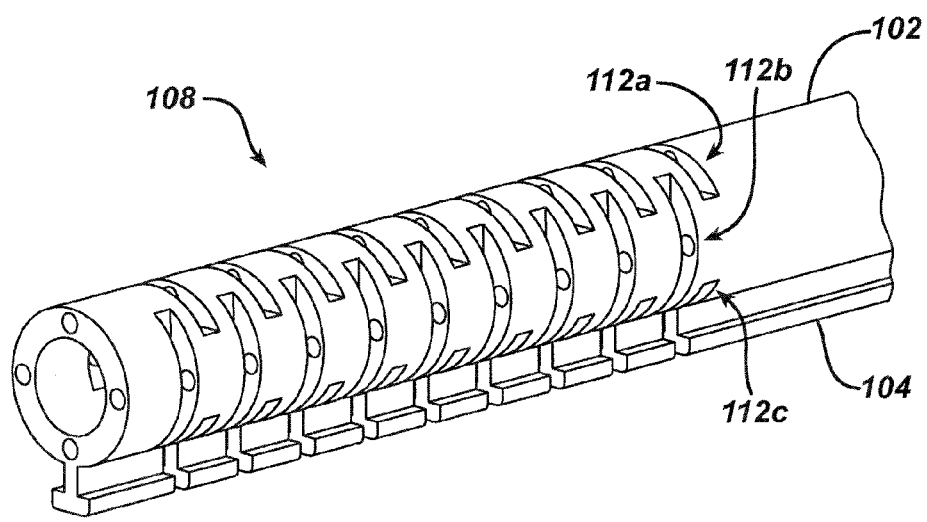
FIG. 8A is a perspective view of a flexible neck of the device shown in FIG. 7.
Figure 8B:
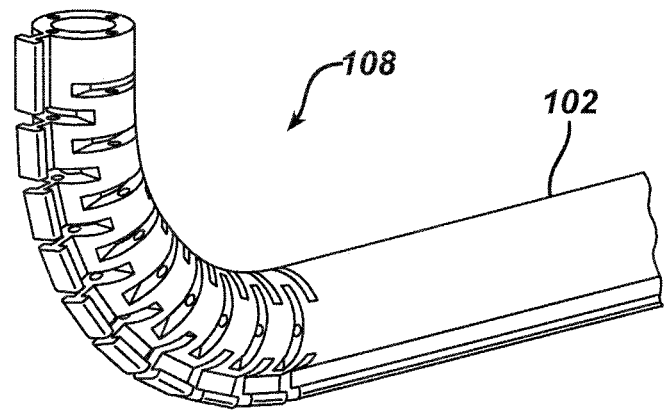
FIG. 8B is a perspective view of the flexible neck shown in FIG. 8A, showing the neck articulated in a first direction.
Figure 8C:
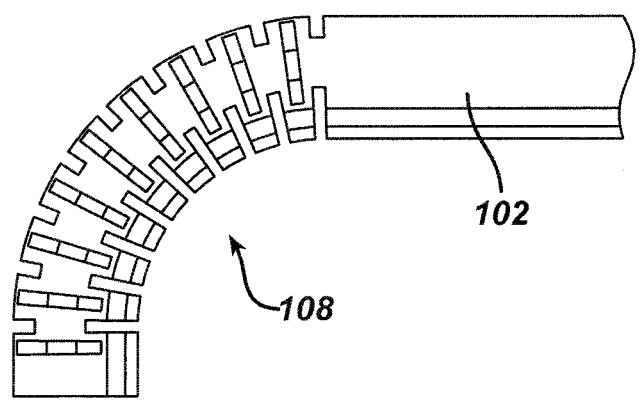
FIG. 8C is a perspective view of the flexible neck shown in FIG. 8A, showing the neck articulated in a second direction.

The flexible neck 108 can have a variety of configurations, and it can be a separate member that is coupled to the elongate shaft 102, or it can be formed integrally with the elongate shaft 102, as shown in FIG. 7. The neck 108 can be made flexible using various techniques. For example, the neck 108 can be formed from one or more segments that move relative to one another, and/or it can be formed from a flexible material. In the exemplary embodiment shown in FIG. 8A, the neck 108 includes several slits 112 formed therein and configured to provide maximum flexibility of the neck 108. While the size, quantity, and orientation of the slits 112 can vary to obtain the desired results, in the illustrated embodiment the flexible neck 108 includes four columns of slits (only three columns of slits, indicated by arrows 112a, 112b, 112c, are shown). Each column extends axially along a length of the flexible neck 108, and each column includes four row of slits spaced radially around circumference of the neck 108. Each column of slits 112 is also axially offset from one another to allow the slits 112 to overlap. In use, when tension is applied to the actuator, the slits 112 will allow the neck 108 to bend or assume a curved configuration such that the neck 108 articulates relative to the remainder of the elongate shaft 102, as shown in FIGS. 8B and 8C.

Figure 9A:
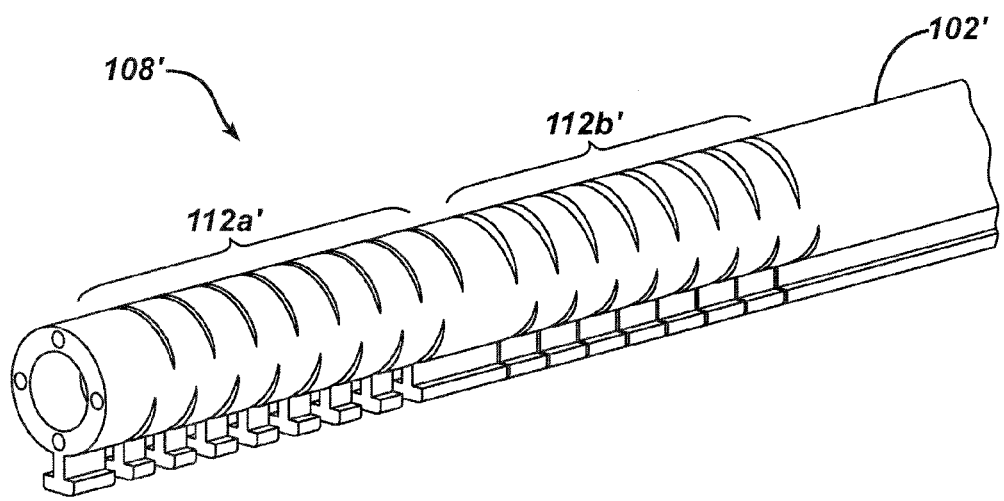
FIG. 9A is a perspective view of another embodiment of a flexible neck for use with an accessory channel.
Figure 9B:
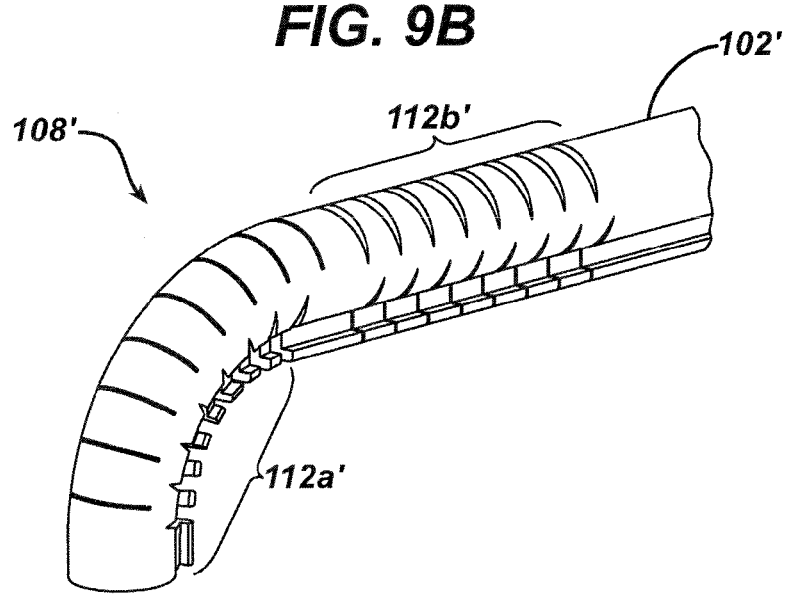
FIG. 9B is a perspective view of the flexible neck shown in FIG. 9A, showing the neck articulated in a first direction.
Figure 9C:
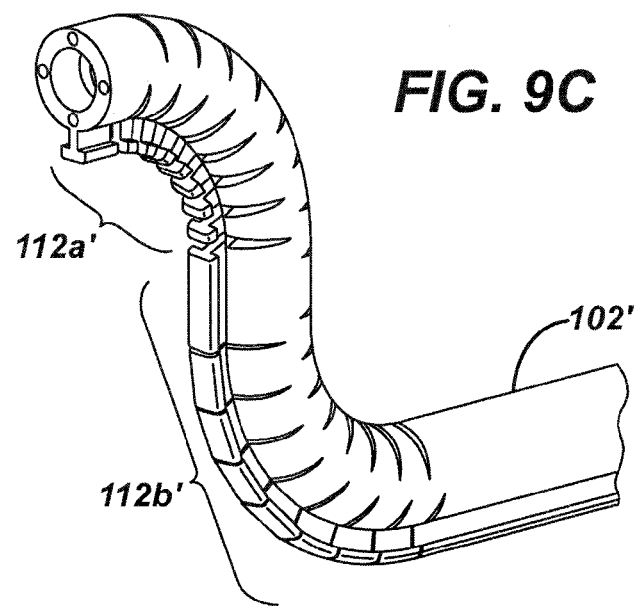
FIG. 9C is a perspective view of the flexible neck shown in FIG. 9A, showing the neck articulated in a second direction.

In other embodiments, the slits can be positioned to allow flexion of the neck at multiple locations or bend points, or to otherwise allow the neck to flex into a predetermined position. By way of non-limiting example, FIG. 9A illustrates another embodiment of a flexible neck 108' having two regions of slits 112' formed therein. In particular, the flexible neck 108' includes a distal region of slits 112a' and a proximal region of slits 112b'. Each region 112a', 112b' can include any number of slits positioned at any location to provide a desired degree of flexibility in one or more desired directions. As shown in FIG. 9A, the proximal end distal regions of slits 112a', 112b' each include two rows of slits formed on opposed sides of and extending along the length of the flexible neck 108'. In use, when tension is applied to the flexible neck 108', as will be discussed in more detail below, the neck 108' will flex at both the proximal and distal regions 112a' 112b' and thereby articulate relative to the remainder of the elongate shaft 102'. As shown in FIG. 9B, flexion can occur first in the distal region 112a' of the neck 108'. Further tension applied to the neck 108' can then cause the proximal region 112b' to flex, as shown in FIG. 9C. In other embodiments, the slits positioning and/or size of the slits can be configured to cause flexion to occur in the proximal region 112b' before it occurs in the distal region 112a', or alternatively the slits can be configured to cause simultaneous flexion of the proximal and distal regions 112b', 112a'. A person skilled in the art will appreciate that the quantity, position, size, and shape of the slits can be adjusted to obtain the desired results. The particular configuration of the cut used to form each slit can also vary. For example, the width and length of the slit can remain constant from an outer surface of the elongate shaft to an inner surface of the elongate shaft, or alternatively the width and length can increase or decrease such that the slit tapers or otherwise varies. By way of non-limiting example, a tapering configuration can be formed by forming a slit having triangular configuration, where the length and width of the slit decrease from the outer surface to the inner surface of the elongate shaft.

As indicated above, the actuator is configured to apply tension to the flexible neck 108 to cause the neck 108 to articulate. The actuator can have a variety of configurations, but in one exemplary embodiment the actuator is similar to the aforementioned actuator and includes one or more cables that extend between the handle 106 and the distal end of the flexible neck 108 such that the handle 106 and the flexible neck 108 are operatively associated. Each cable can be configured to apply tension to the flexible neck 108 to cause the neck 108 to articulate in a plane of motion. Thus, where the device 100 includes only one cable, the flexible neck 108 can articulate in a single plane of motion. Each additional cable can allow the neck 108 to articulate in a different plane of motion. Where multiple cables are provided, the neck 108 can articulate in multiple planes of motion. Moreover, the cables can be simultaneously tensioned, potentially allow for 360° articulation of the flexible neck 108.

Figure 10:
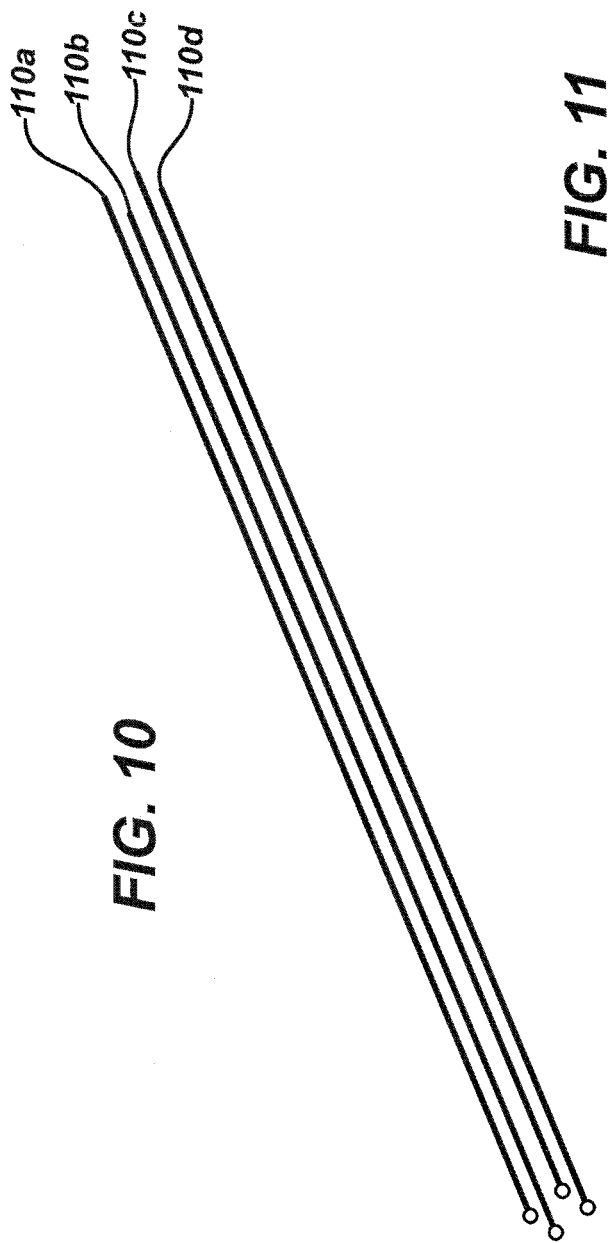
FIG. 10 is a perspective view of a plurality of cable actuators for use with the device of FIG. 7.
Figure 11:
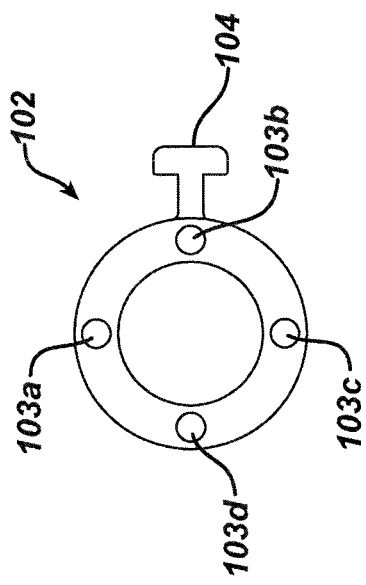
FIG. 11 is a cross-sectional view of a shaft of the accessory channel of FIG. 7.

While the number of cables can vary, and the device 100 can include only one cable, in the embodiment shown in FIG. 7 the device 100 includes four cables (only three cables 110a, 110b, 110c are shown). A portion of the cables 110a, 110b, 110c, 110d is shown in more detail in FIG. 10. As noted above, the cables 110a-d extend along a length of the elongate shaft 102 between the handle 106 and the flexible neck 108. The particular location of the cables 110a-d can vary, but in an exemplary embodiment the cables 110a-d are spaced radially around a circumference of the elongate shaft 102 and they extend between the distal-most end of the flexible neck 108 and the handle 106. The cables 110a-d can extend internally through or externally along the elongate shaft 102, or they can extend through lumens or pathways formed in the sidewall of the elongate shaft 102. FIG. 11 illustrates a cross-sectional view of the elongate shaft 102, showing four lumens 103a, 103b, 103c, 103d formed therein. The lumens 103a-d preferably have a size that allows the cables 116a-d to slide therein, and they are spaced circumferentially about the elongate shaft 102. The lumens 103a-d extend between the proximal and distal ends 102a, 102b of the elongate shaft 102 to allow the cables 110a-d to extend between the handle 106 and the distal-most end of the flexible neck 108.

Figure 12:
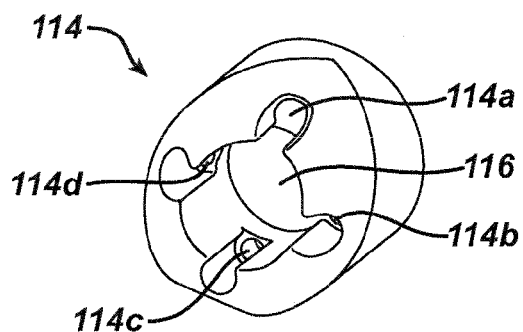
FIG. 12 is a perspective view of one embodiment of an end cap for use with the accessory channel of FIG. 7.

The distal end of the cables 110a-d can mate to the distal most end of the flexible neck 108 using a variety of techniques, but in one embodiment, shown in FIG. 12, the flexible neck 108 includes an end cap 114 coupled to or formed on the distal-most end thereof. While the configuration of the end cap 114 can vary depending on the configuration of the actuator, in the illustrated embodiment the end cap 114 includes four bores 114a, 114b, 114c, 114d formed therein and spaced around a circumference of the end cap 114 such that the bores 114a-d align with the lumens 103a-d in the elongate shaft 102. Each bore 114a-d is configured to receive one of the cables 110a-d. Various mating techniques can be used to retain the cables 110a-d within the bores 114a-d. For example, FIG. 10 illustrates ball formed on the end of each cable 110a-d for retaining the ends of the cables 110a-d in the bores 114a-d in the end cap 114. The end cap 114 can also include a central lumen 116 formed therein for receiving a tool therethrough. The lumen 116 can also function to facilitate positioning of a tool inserted through the accessory channel 100.

The proximal end of the cables 110a-d can be mated to a handle 106 that is coupled to a proximal end of the shaft 102. While the handle 106 can have a variety of configurations, in one exemplary embodiment, previously shown in FIG. 7, the handle 106 can be in the form of a joystick that is movably coupled to the proximal end 102a of the elongate shaft 102, and in particular that is configured to articulate relative to the proximal end 102a of the elongate shaft 102. The articulating movement of the handle 106 can allow the motion of the handle 106 to be mimicked by the flexible neck 108, as will be discussed below.

Figure 13A:
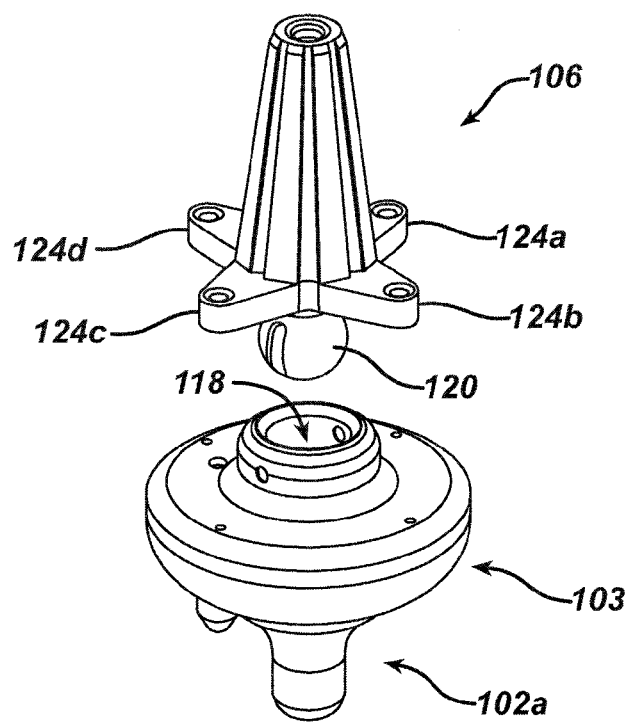
FIG. 13A is an exploded view of the handle and a proximal portion of the elongate shaft of the device shown in FIG. 7.

While articulating movement can be achieved using a variety of types of joints, in the illustrated embodiment a ball-and-socket connection is formed between the handle 106 and the elongate shaft 102. In particular, as shown in more detail in FIGS. 13A and 13B, the proximal end 102a of the elongate shaft 102 includes a housing 103 formed thereon and defining a socket 118 in a proximal end thereof. The handle 106 includes a ball 120 that is movably disposed within the socket 118, and the joystick extends proximally from the ball 120 thus allowing the handle 106 to articulate relative to the elongate shaft 102. A pin or other mechanism can be used to movably retain the ball 120 within the socket 118. A person skilled in the art will appreciate that the handle can have a variety of other shapes, and that various other techniques can be used to movably connect the handle 106 to the elongate shaft 102.

As indicated above, the proximal end of the cables 110a-d is configured to mate to the handle 106. Thus, the handle 106 can include features for mating to the cables 110a-d. While the particular mating features can vary depending on the configuration of the actuator, in an exemplary embodiment the joystick 122 on the handle 106 includes four legs 124a, 124b, 124c, 124d formed thereon. The legs 124a-d are spaced around a circumference of the joystick 122, such that they are substantially aligned with the cables, and each leg 124a-d is configured to mate to a terminal end of one of the cables 110a-d. A ball-and-socket connection, as previously described with respect to the distal ends of the cables 110a-d, can be used to mate the cables 110a-d to the legs, or alternatively any other mating technique known in the art can be used.

Figure 13B:
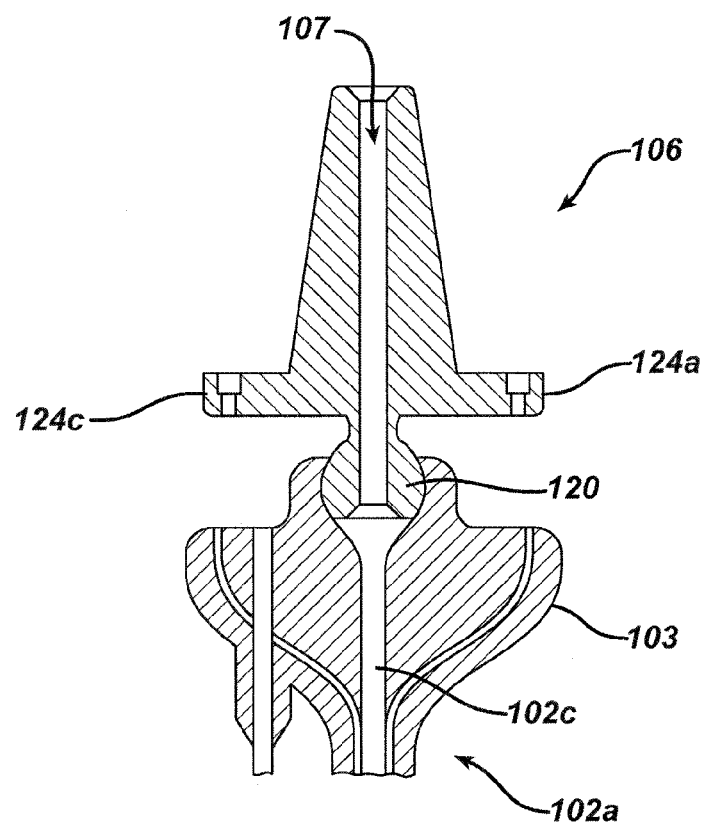
FIG. 13B is a cross-sectional view of the handle and the proximal portion of the elongate shaft of FIG. 13A in an assembled configuration.

Referring back to FIG. 7, in use the handle 106 can be pivoted or angularly oriented relative to the proximal end 102a of the elongate shaft 102 to effect mimicking movement of the flexible neck 108, and to thereby position a tool extending through the flexible neck 108. As shown in FIGS. 7 and 13B, the joystick on the handle 106 can include a lumen 107 formed therethrough and axially aligned with the lumen 102c in the elongate shaft 102 for allowing a tool to be introduced through the device 100. In other embodiments, the handle 106 can be offset from the proximal end 102a of the elongate shaft 102 such that the handle 106 is coupled to the cables, but does not interfere with direct access to the lumen 102c in the elongate shaft 102.

In order to control movement of the flexible neck 108 and thus a tool positioned therethrough, the handle 106 is pivoted or articulated about the proximal end 102a of the elongate shaft 102. For example, movement of the handle 106 in a first direction will cause the legs 124a-d on the handle 106 to apply a force to one or more of cables 110a-d to pull the cable(s) axially. As a result, the actuated cables will apply a tension force to the flexible neck 108 to cause the neck 108 to flex. In order to prevent the elongate shaft 102 from flexing in response to tension applied to the cables 110a-d by the handle 106, the flexible neck 108 can have a greater flexibility than the elongate shaft 102. This can be achieved, for example, using the slits as previously described, or in other embodiments the shaft 102 can include a stabilizing element, such as a rod, extending therethrough to make the shaft 102 more rigid than the flexible neck 108. The direction of movement of the handle 106 will be mimicked by the flexible neck 108, either in the same direction (i.e., corresponding movement) or in an opposite direction (i.e., mirrored movement), thus allowing a user to precisely control the position of the flexible neck 108, and thus to control the position of a tool extending through the flexible neck 108. In an exemplary embodiment, the particular amount of movement of the flexible neck 108 can be proportional to the amount of movement of the handle 106. That is, the amount of movement of the flexible neck 108 can be directly equivalent to the amount of movement of the handle 106, or it can be proportionally increased or decreased relative to the amount of movement of the handle 106. In certain embodiments, it may be desirable to have the amount of movement of the flexible neck 108 be increased relative to the amount of movement of the handle 106. As a result, only small movements of the handle 106 will be necessary to allow large movements of the flexible neck 108. While various techniques can be achieved to proportionally multiple or increase the movement of the flexible neck 108, one exemplary embodiment of a force multiplying mechanism is an eccentric cam that is coupled to the cables and that increases the mechanical advantage, either force or displacement, of the cables 110a-d as tension is applied to the cables 110a-d by the handle 106.

As previously explained, while the movement between the handle and the working end of the device can be proportional in theory, in practice some lose of force will likely occur as the force is transferred through the elongate shaft. Accordingly, proportional movement as used herein is intended to include applications in which the handle and working end are configured to move in proportionate amounts, but in which some lose of force may occur during actual operation of the device.

Figure 14A:
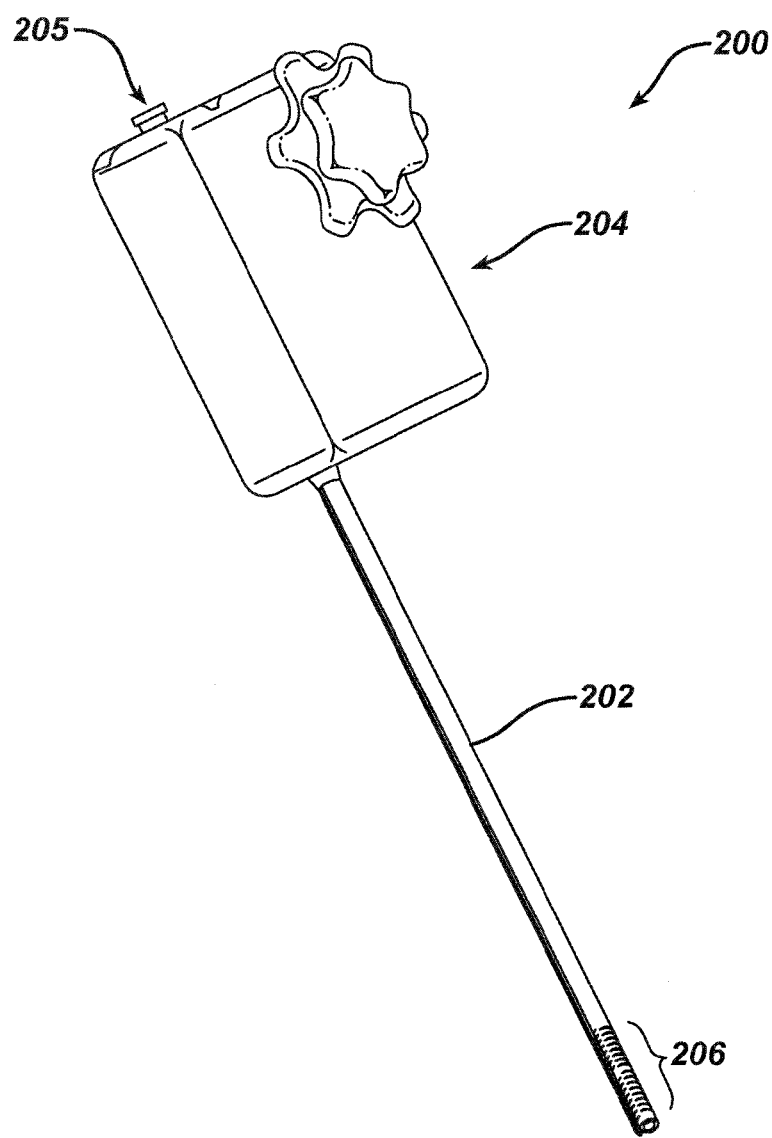
FIG. 14A is a perspective view of another embodiment of an accessory channel.
Figure 14B:
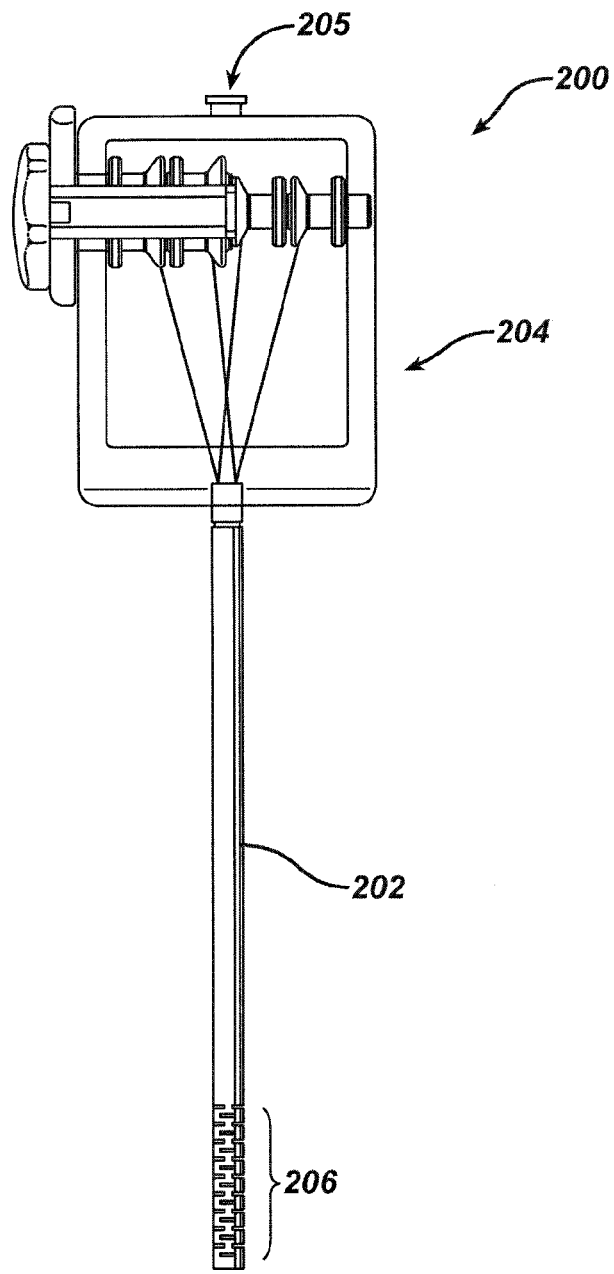
FIG. 14B is a cross-sectional view of the accessory channel shown in FIG. 14A.

While FIGS. 1A and 7 illustrate devices in which the working end mimics movement of the handle, the handle can have a variety of other configurations in which it is effective to articulate the working end of the device without having the working end of the device mimic movement of the handle. FIGS. 14A and 14B illustrate another embodiment of a device 200 having a handle 204 that includes a rotatable member that is effective to articulate a flexible neck 206 in one or more planes of motion relative to an elongate shaft 202 of the device. In general, the elongate shaft 202 of the device 200 is very similar to the elongate shaft 102 previously described, and it generally includes a flexible neck 206 coupled to or formed on a distal end thereof. Four cable actuators (not shown) extend through the elongate shaft between the handle 106 and the flexible neck 206. The shaft 102 and the cable actuators are similar to the shaft 102 and cable actuators 110a-d previously described with respect to device 100, and thus they will not be described in detail.

Figure 15A:
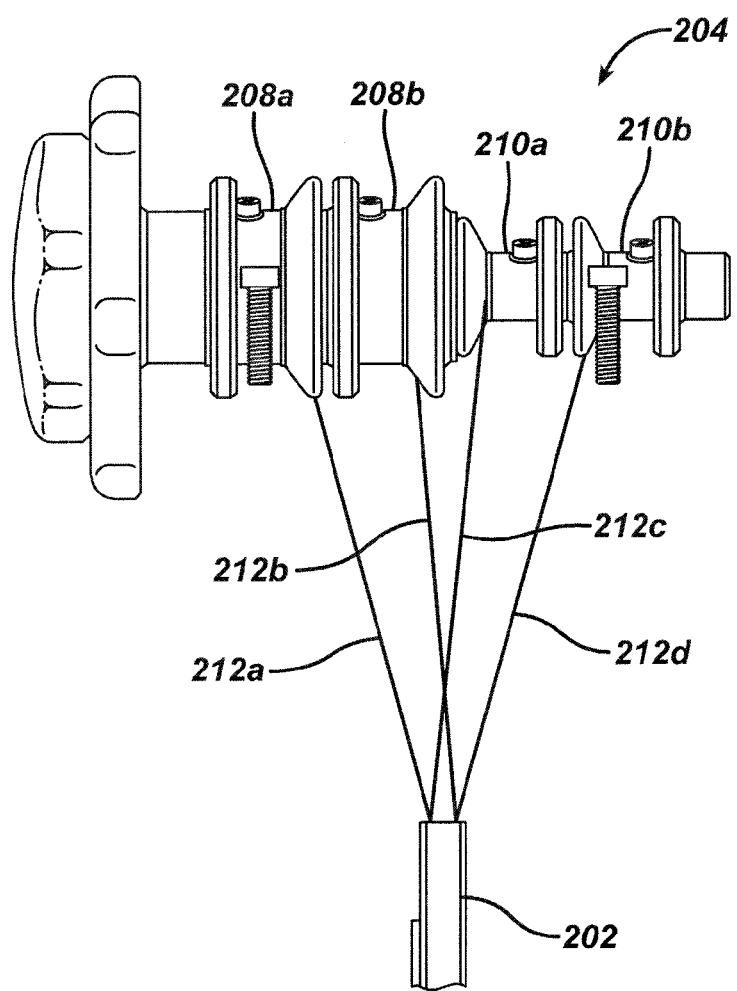
FIG. 15A is a side view of a handle assembly of the device shown in FIGS. 14A and 14B.
Figure 15B:
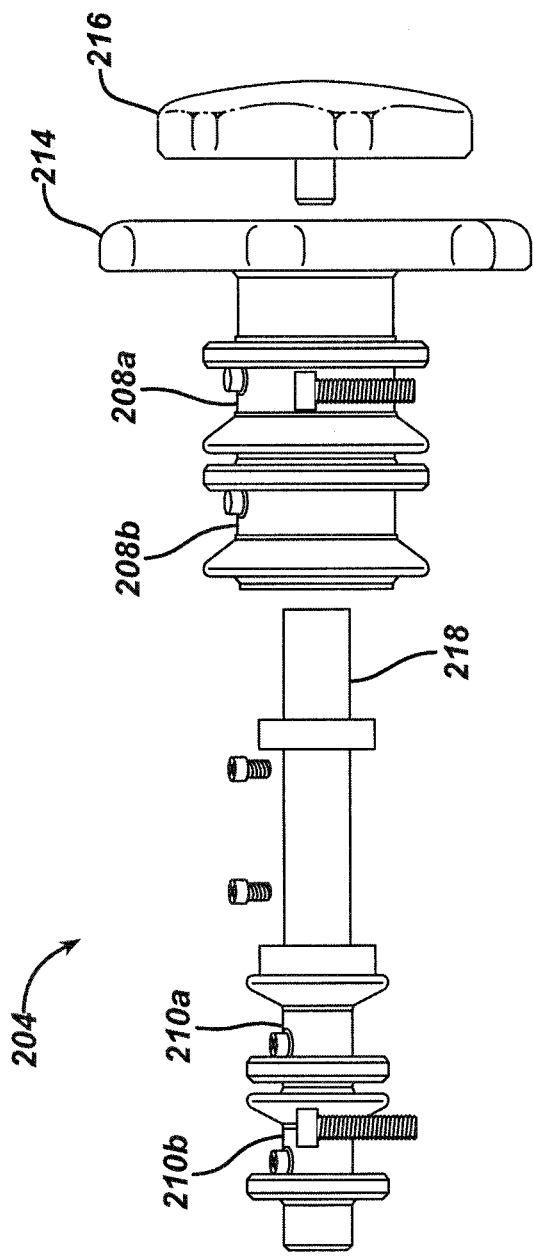
FIG. 15B is an exploded view of the handle assembly of FIG. 15A.

The handle 204 of the device 200 is shown in more detail in FIGS. 15A and 15B. In general, the handle 204 includes one or more spools rotatably disposed therein. Each spool is configured to mate to and control one of the cable actuators. Thus, rotation of each spool will wind up or release the cable, thereby causing the flexible neck 108 to flex and articulate in a particular direction. While the number of spools can vary depending on the number of cable actuators, in the embodiment shown in FIGS. 15A and 15B, the handle 204 includes four spools 208a, 208b, 210a, 210b. The first two spools 208a, 208b are coupled to one another, and the second two spools 210a, 210b are coupled to one another. A first cable 212a is coupled to and wound around the first spool 208a, and a second cable 212b is coupled to and wound around the second spool 208b. The first and second cables 212a, 212b are positioned on and extend along opposite sides of the elongate shaft 202. As a result, tension applied to the first cable 212a will cause the flexible neck 206 to articulate in direction within a first plane of motion, and tension applied to the second cable 212b will cause the flexible neck 206 to articulate in the opposite direction within the same plane of motion.

To allow tension to be applied to only one of the cables 212a, 212b, the first and second cables 212a, 212b are wound around the first and second spools 208a, 208b in opposite directions. Thus, rotation of the first and second spools 208a, 208b will wind and apply tension to one of the cables 212a, 212b while unwinding and releasing tension on the other one of the cables 212a, 212b. Third and fourth cables 212c, 212d are likewise wound around the third and fourth spools 210a, 210b such that rotation of the third and fourth and second spools 210a, 210b will wind and apply tension to one of the cables 212c, 212d while unwinding and releasing tension on the other one of the cables 212c, 212d. The third and fourth cables 212c, 212d can extend along the shaft 102 at a position that is radially offset from the first and second cables 212a, 212b such that the third and fourth cables 212c, 212d cause articulation of the flexible neck 206 in a second, different plane of motion. For example, the third and fourth cables 212c, 212d can be offset from the first and second cables 212a, 212b by about 90° such that the cables 212a-d are all spaced substantially equidistant around the circumference of the elongate shaft 202. A person skilled in the art will appreciate that the handle 204 can include any number of spools and cables to effect articulation in a desired number of planes.

In order to control the spools 208a, 208b, 210a, 210b, the device can include one or more grasping members. As shown in FIGS. 15A and 15B, a first rotatable knob 214 is coupled to the first and second spools 208a, 208b, and a second rotatable knob 216 is coupled to the third and fourth spools 210a, 210b. The knobs 214, 216 can be integrally formed with the spools 208a, 208b, 210a, 210b, or they can be coupled to the spools 208a, 208b, 210a, 210b by a shaft that extends through the spools 208a, 208b, 210a, 210b. In the illustrated embodiment, the first knob 214 is formed on or coupled directly to the first spool 208a, and the second knob 216 is coupled to the third and fourth spools 210a, 210b by a shaft 218 that extends from the knob 216 through the first and second spools 208a, 208b, and that couples to the third and fourth spools 210a, 210b. In other words, the first and second spools 208a, 208b are rotatably disposed around the shaft 218.

In certain exemplary embodiments, the spools and the rotatable knobs can also differ in size. In the embodiment shown in FIGS. 15A and 15B, the first and second spools 208a, 208b, as well as the first rotatable knob 214, have a diameter that is greater than a diameter of the third and fourth spools 210a, 210b and the second rotatable knob 216. While not necessary, such a configuration can be advantageous as it spaces the cables 212a-d apart to prevent the cables 212a-d from coming into contact with one another.

In use, a tool can be positioned through the elongate shaft 202, and the knobs 214, 216 can be rotated to articulate the flexible neck 206 on the shaft 202 and thereby position the tool as desired. As shown in FIGS. 14A and 14B, the handle 204 can include a lumen 205 extending therethrough and in alignment with the lumen in the elongate shaft 202 for allowing a tool to be passed through the handle 204 and the shaft 202. In other embodiments, the handle 204 can be offset from the elongate shaft 202 to provide direct access to the lumen in the elongate shaft 202. Once the tool is positioned through the shaft 202, the knobs 214, 214 can be rotated to articulate the flexible neck 206 on the distal end of the elongate shaft 202. In particular, the first knob 214 can be rotated in a first direction, e.g., clockwise, to apply tension to one of the cables, e.g., the first cable 212a, while releasing or unwinding the other cable, e.g., the second cable 212b. As a result, the tension applied to the first cable 212a will pull the distal-most end of the flexible neck 206 in a proximal direction, causing the flexible neck 206 to flex and thereby articulate in a first direction. Rotation of the first knob 214 in an opposite direction, e.g., counterclockwise, will unwind the first cable 212a while winding the second cable 212b. The flexible neck 206 will return to its initial, linear configuration. Further rotation of the first knob 214 will continue to wind the second cable 212b while unwinding the first cable 212a, thereby causing the flexible neck 206 to flex and articulate in an opposite direction along the same plane of motion. The second knob 216 can be likewise rotated to articulate the flexible in a different plane of motion. The knobs 214, 216 can also optionally be rotated simultaneously to articulate the flexible neck 206 in additional planes of motion different than the first and second planes of motion.

Figure 16A:
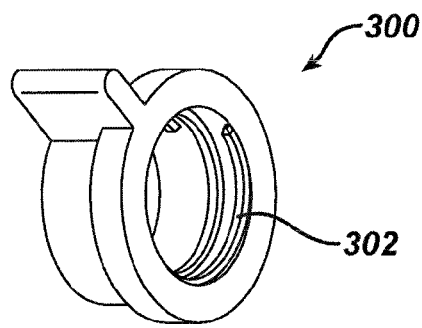
FIG. 16A is a perspective view of one embodiment of a locking mechanism.
Figure 16B:
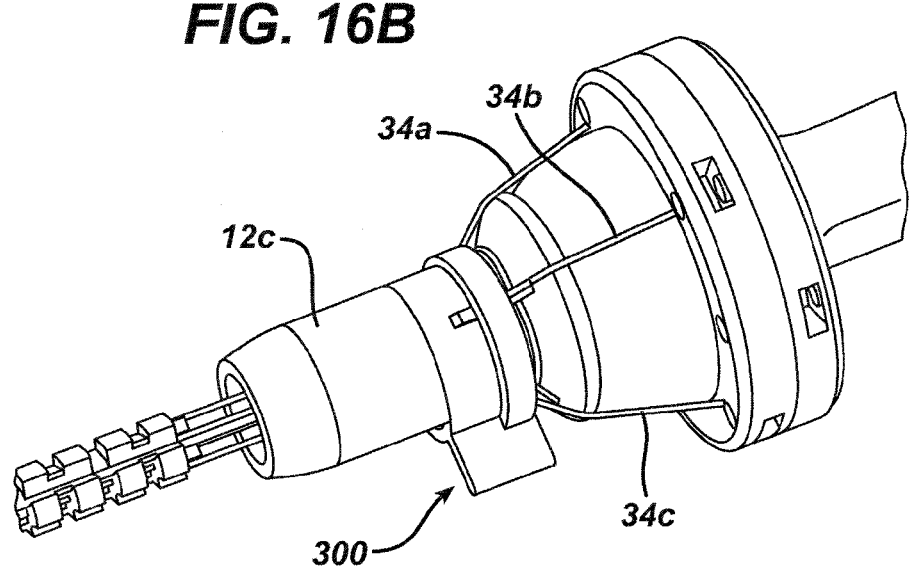
FIG. 16B is a perspective view of the locking mechanism of FIG. 16A coupled to the surgical stapling and cutting device of FIGS. 1A and 1B.

In other embodiments, the various devices disclosed herein can include a locking mechanism for locking the handle(s) and/or actuator in a fixed position to maintain the working end of a device in desired articulated or angular orientation. While the locking mechanism can have a variety of configurations, in one exemplary embodiment the locking mechanism can be in the form of a clamp that is effective to clamp down onto the cables and thereby prevent movement of the cables to lock the working end in a desired orientation. The clamp can have a variety of shapes and sizes, and it can be positioned at various locations on the device. FIGS. 16A and 16B illustrate one exemplary embodiment of a clamp 300 that is disposed around the hollow housing 12c on the surgical fastening and cutting device 10 of FIGS. 1A and 1B. The clamp 300 is generally ring-shaped and can be configured to be slidably or rotatably mated to the hollow housing 12c adjacent to the openings through which the cables (only three cables 34a, 34b, 34c are shown in FIG. 16B) extend. In an initial position, the clamp 300 is spaced apart from the openings to allow free movement of the cables 34a-d therethrough. Once the working end of the device, e.g., the end effector 16, is articulated into a desired position, the clamp 300 can moved axially along the hollow housing 12c until it extends over the openings and engages the cables 34a-d extending therefrom. The clamp 300 will thus prevent movement of the cables 34a-d when the clamp 300 is in the locked position. In order to move the clamp 300 axially and to lock the clamp 300 to the housing 12c, the clamp 300 can include a mating element formed thereon and configured to engage a corresponding mating element formed on the housing 12c. As shown in FIGS. 16A and 16B, the clamp includes threads 302 formed therein that are configured to mate with corresponding threads (not shown) formed on the housing 12c. As a result, rotation of the clamp 300 about the housing 12c will cause the clamp 300 to move between the initial and locked positions. A person skilled in the art will appreciate that various other mating techniques can be used. Moreover, the locking mechanism can have a variety of other configurations. For example, the handle can include a locking element formed thereon and configured to lock the handle in a fixed, articulated position.

In other embodiments, the cables can be used to passively allow articulation of the elongate shaft through a body lumen, and the clamp 300 or other locking mechanism can be used to lock the working end of the device into position when desired. In such a configuration, the handle can merely be used to facilitate grasping of the device.

In other embodiments, the cable actuators disclosed herein used to effect articulation of a working end of a device can be formed from an electroactive polymer material. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction. Thus, the cable actuators previously disclosed herein can be replaced by EAP actuators, and the handle can be configured to activate an energy source to selectively deliver energy to one or more of the cables. In an exemplary embodiment, movement of the handle can be configured to dictate the amount of the energy source, as well as the cable(s) receiving the energy source. As a result, movement of the handle can still be mimicked by the working end of the device to provide the user with the same, precise control over the position of the working end. The energy source can be an internal source, such as a battery, or it can be an external source. In other embodiments, the EAP cable actuators can supplement the axial force applied to the cables by movement of the handle and thereby proportionally increase the amount of movement of the working end relative to the handle.

In other aspects, the cable actuators can be formed from a shape-memory material, such as Nitinol. Such a configuration allows tension to be applied to the cables to articulate the end effector, yet allows the cables to return to an initial linear configuration without having to manipulate the handle.

In yet another embodiment, the various devices disclosed herein, including portions thereof, can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. By way of example, the surgical stapling and fastening device shown in FIGS. 1A and 1B can be reconditioned after the device has been used in a medical procedure. The device can be disassembled, and any number of the particular pieces can be selectively replaced or removed in any combination. For example, for the surgical stapling and cutting device, a cartridge disposed within the end effector and containing a plurality of fasteners can be replaced by adding a new fastener cartridge to the end effector. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    an elongate shaft having a proximal end with a handle movably coupled thereto, and a distal end having a flexible neck extending therefrom with an end effector coupled to a distal end of the flexible neck, wherein the handle and the flexible neck are operatively associated such that movement of the handle is mimicked by the flexible neck; and
    a rotating member coupled to the handle, wherein the rotating member is configured to rotate relative to the handle in a distal position to effectuate rotation or actuation of the end effector, wherein the rotating member is configured to be retracted from the distal position to a proximal position relative to the handle, wherein the rotating member is configured to rotate relative to the handle in the proximal position to effectuate the other of rotation or actuation of the end effector, and wherein actuation fires at least one fastener from the end effector, causes the end effector to cut tissue, or both fires at least one fastener from the end effector and causes the end effector to cut tissue.

2. The device of claim 1, wherein the mimicking movement is proportional.

3. The device of claim 1, wherein the handle is adapted to articulate relative to the proximal end of the elongate shaft.

4. The device of claim 3, wherein the handle is coupled to the proximal end of the elongate shaft by a joint selected from the group consisting of a ball and socket joint, a hinge joint, and a flexing joint.

5. The device of claim 1, wherein the handle and the flexible neck are operatively associated by an actuator extending between the handle and the flexible neck, the actuator being configured to transfer movement from the handle to the flexible neck.

6. The device of claim 5, wherein the actuator comprises at least one cable extending along a length of the elongate shaft and effective to apply a force to the flexible neck to move the flexible neck in at least one plane of motion.

7. The device of claim 6, wherein the at least one cable is formed from an electroactive polymer material, and wherein movement of the handle is effective to selectively deliver energy to the at least one cable to cause the at least one cable to axially contract and radially expand and thereby cause at least one of the flexible neck to mimic the motion of the handle.

8. The device of claim 6, wherein the at least one cable comprises a plurality of cables extending along a length of the elongate shaft, each cable being effective to apply a force to the flexible neck to move the flexible neck in a different plane of motion.

9. The device of claim 8, wherein the plurality of cables are equally spaced apart from one another around a circumference of the actuator.

10. The device of claim 8, wherein the plurality of cables comprise at least three cables extending along a length of the elongate shaft.

11. The device of claim 8, wherein at least one of the handle and the plurality of cables include a locking mechanism associated therewith and configured to maintain at least one of the handle and the plurality of cables in a fixed position.

12. The device of claim 1, wherein the elongate shaft includes a central lumen extending therethrough along a length thereof, the central lumen being adapted to receive a tool therethrough.

13. The device of claim 12, wherein the elongate shaft includes a mating element formed on and extending along a length of an external surface thereof for mating to a complementary mating element formed on a sleeve adapted to receive an endoscope.

14. A surgical device, comprising:
    an elongate shaft having a proximal end and a distal end with a flexible neck defining a working end of the device and having an end effector coupled thereto, the flexible neck being made flexible by a plurality of slits formed therein;

a handle movably coupled to the proximal end of the elongate shaft and operatively associated with the flexible neck such that movement of the handle is effective to cause the flexible neck to articulate in multiple planes;

a rotating member coupled to the handle and being movable in a proximal direction relative to the elongate shaft from a first position relative to the elongate shaft to a second position relative to the elongate shaft, the rotating member being rotatable relative to the elongate shaft while remaining in the first position relative to the elongate shaft to rotate the end effector, and the rotating member being rotatable relative to the elongate shaft while remaining in the second position relative to the elongate shaft to actuate the end effector, wherein actuation fires at least one fastener from the end effector, causes the end effector to cut tissue, or both fires at least one fastener from the end effector and causes the end effector to cut tissue; and a translating member coupled to the handle and being effective to move the rotating member between the first and second positions.

15. The device of claim 14, wherein the handle is operatively associated with the flexible neck by a plurality of cables spaced circumferentially about the elongate shaft and extending between the handle and a distal end of the flexible neck, the plurality of cables being configured to slide relative to an axis of the elongate shaft in response to movement of the handle and to tension the flexible neck to cause the flexible neck to articulate.

16. The device of claim 15, further comprising a locking mechanism positioned to engage at least one of the handle and the plurality of cables to lock the handle and the plurality of cables in a fixed position and thereby maintain the flexible neck in a fixed position.

17. A surgical device, comprising:
a flexible elongate shaft having proximal and distal ends, the distal end having an end effector coupled thereto;
a plurality of cables spaced circumferentially about the elongate shaft and extending between the proximal and distal ends of the elongate shaft, the plurality of cables being configured to slide relative to an axis of the elongate shaft and to apply tension to the elongate shaft to cause at least a portion of the elongate shaft to flex and bend;
a rotating member that is movable in at least one of proximal and distal directions relative to the elongate shaft along a longitudinal axis of the elongate shaft, wherein the rotating member is effective to rotate about the longitudinal axis of the elongate shaft to selectively rotate and actuate the end effector, wherein actuation fires at least one fastener from the end effector, causes the end effector to cut tissue, or both fires at least one fastener from the end effector and causes the end effector to cut tissue; and a locking mechanism coupled to the elongate shaft and positioned to engage the plurality of cables to lock the plurality of cables in a fixed position and thereby maintain the elongate shaft in a fixed position.

18. The device of claim 17, wherein the elongate shaft is configured to passively flex and bend when it is inserted through a tortuous lumen.

19. A surgical method, comprising:
inserting an elongate shaft into a body lumen to position a flexible neck coupled to a distal end of the elongate shaft adjacent to tissue to be treated, a distal end of the flexible neck having an end effector coupled thereto;

moving a handle pivotally coupled to a proximal end of the elongate shaft to cause the flexible neck to mimic the motion of the handle;

selecting one of first and second positions for a rotating member, the second position being retracted from the first position at a different axially-aligned position than the first position along a longitudinal length of the elongate shaft; and rotating the rotating member relative to the elongate shaft in the selected one of the first and second positions, wherein rotating the rotating member in the first position causes rotation of the end effector and rotating the rotating member in the second position causes at least one of firing at least one fastener from the end effector, and cutting tissue engaged by the end effector.

20. The method of claim 19, wherein the mimicking motion is proportional.

21. The method of claim 19, wherein the flexible neck mirrors movement of the handle.

22. The method of claim 19, wherein movement of the flexible neck directly corresponds to movement of the handle.

23. The method of claim 19, wherein the handle is pivotally articulated about the proximal end of the elongate shaft to cause the flexible neck to mimic the motion of the handle.

24. The method of claim 19, wherein inserting the elongate shaft comprises mating the elongate shaft to a sleeve disposed around an endoscope, and sliding the elongate shaft along the sleeve to position the flexible neck adjacent to a distal end of the endoscope.

25. The method of claim 24, further comprising inserting a tool through a central lumen formed in the elongate shaft to position a working end of the tool in proximity to a distal end of the flexible neck such that moving the handle pivotally coupled to a proximal end of the elongate shaft causes the working end of the tool to move as the flexible neck proportionally mimics the motion of the handle.

* * * * *